(12) United States Patent
Sase

(10) Patent No.: US 6,337,895 B1
(45) Date of Patent: Jan. 8, 2002

(54) METHOD FOR DETERMINING CONSTANT IN RELATIONAL EXPRESSION CONCERNING END-TIDAL AIR VELOCITY CONSTANT AND ARTERIAL BLOOD VELOCITY CONSTANT AND XENON CT APPARATUS

(75) Inventor: Shigeru Sase, Narashino (JP)

(73) Assignee: Anzai Medical Kabushiki Kaisha, Tokyo (JP)

(*) Notice: Subject to any disclaimer, the term of this patent is extended or adjusted under 35 U.S.C. 154(b) by 0 days.

(21) Appl. No.: 09/630,544

(22) Filed: Aug. 1, 2000

(30) Foreign Application Priority Data

Mar. 30, 2000 (JP) ............................................ 12-093636

(51) Int. Cl.⁷ ................................................. A61B 6/03
(52) U.S. Cl. ............................................. 378/8; 378/18
(58) Field of Search ........................... 378/4, 8, 18, 901

(56) References Cited

U.S. PATENT DOCUMENTS 4,535,780 A * 8/1985 Gur et al. .................... 600/436
4,610,258 A * 9/1986 Colsher ....................... 600/504

FOREIGN PATENT DOCUMENTS

| DE | 35 22 113 A1 | 1/1986 |
| JP | 3-33326 | 5/1991 |
| WO | WO 90/11045 | 10/1990 |

OTHER PUBLICATIONS

Shigeru Sase, "The Effect of Xenon Inhalation Speed on Cerebral Blood Flow Obtained Using the End–Tidal Method in Xenon–Enhanced CT," J. Computer Assisted Tomography 22(5):786–791 (1998).

N. Veall et al., "The Partition of Trace Amounts of Xenon Between Human Blood and Brain Tissues at 37 deg. C," Phys. Med. Bio., vol. 10, No. 3, pp. 375–380 (1965).

Shimoda et al., "Discrepancy of xenon concentrations between end–tidal and blood collection methods in xenon–enhanced computed tomographic measurement of cerebral blood flow," Neuroradialogy 35:66–8 (1992).

Communicationand copy of Search Report from the European Patent Office (EPO).

DE 35 22 113 A1 correspondsto U.S. Patent No. 4,718,432, a copy of which is attached to serve as the translation thereof.

* cited by examiner

Primary Examiner—David V. Bruce
(74) Attorney, Agent, or Firm—Paul A. Guss

(57) ABSTRACT

It is intended to correctly determine the cerebral blood flow in a successful manner. When a constant $\gamma$ is determined in a relational expression of $\{Ka=\gamma \times (1-\exp(-Ke/\gamma))\}$ provided that Ke represents an end-tidal air velocity constant and Ka represents an arterial blood velocity constant concerning a xenon CT examination, a K-S-calculating means determines a temporary calculated value $\lambda\alpha$ of a brain/blood distribution coefficient $\lambda$ from temporary calculated values $Ka_i\alpha$, $Ka_o\alpha$ obtained by a Ke/Ka conversion means on the basis of an assumed value $\gamma\alpha$ of the Ke/Ka conversion constant $\gamma$ set by an assumed value-setting means. In this case, the assumed value-setting means varies the assumed value $\gamma\alpha$ within a desired range. A $\gamma$ value-establishing means establishes, as a true Ke/Ka conversion constant $\gamma$, the assumed value $\gamma\alpha$ obtained when the temporary calculated value $\lambda\alpha$ most closely approaches a target value $\lambda\tau$ by comparing the temporary calculated value $\lambda\alpha$ with the target value $\lambda\tau$ from a target $\lambda$ value-calculating means.

15 Claims, 21 Drawing Sheets

METHOD FOR DETERMINING CONSTANT IN RELATIONAL EXPRESSION CONCERNING END-TIDAL AIR VELOCITY CONSTANT AND ARTERIAL BLOOD VELOCITY CONSTANT AND XENON CT APPARATUS

BACKGROUND OF THE INVENTION

1. Field of the Invention

The present invention relates to a method for determining a constant in a relational expression concerning the end-tidal air velocity constant and the arterial blood velocity constant, and a xenon CT apparatus. In particular, the present invention relates to a method for determining a constant in a relational expression concerning the end-tidal air velocity constant and the arterial blood velocity constant, and a xenon CT apparatus which make it possible to correctly measure the cerebral blood flow rate by utilizing, for example, a xenon gas supply unit and an X-ray CT unit.

2. Description of the Related Art

A method is known, for example, in which a tomographic image of a head of a patient as a specimen is obtained by using an X-ray CT apparatus, while the patient is allowed to inhale a mixed gas composed of xenon gas and oxygen gas fed from a gas inhalation unit for a certain period of time by the aid of a breathing mask, and then the patient is allowed to breathe ordinary air, wherein the tomographic image is analyzed to measure the blood flow in the head of the patient.

That is, according to this measuring method, the mixed gas is absorbed into the pulmonary vein from the lungs of the patient, it passes through the heart, and it flows as the arterial blood flow into the tissue of the head. The mixed gas passes through the head tissue, it returns to the heart via the venous blood flow, and it is returned to the pulmonary artery via the heart. During this process, the time-dependent change of the xenon gas concentration in the tissue of the head is observed by using the X-ray CT apparatus, and it is compared with the time-dependent change of the xenon gas concentration of a head in which the tissue is normal. Thus, it is possible to diagnose the head of the patient.

In order to obtain the cerebral blood flow rate by using the measuring method described above, it is necessary to obtain the xenon gas concentration in the artery together with the xenon gas concentration in the cerebral tissue. Recently, the xenon gas concentration in the end-tidal air, which can be detected by a noninvasive method, is substitutively used as the xenon gas concentration in the artery.

The inventors of this application have found out and revealed the correlation between the xenon gas concentration in the artery and the xenon gas concentration in the end-tidal air {see "The Effect of Xenon Inhalation Speed on Cerebral Blood Flow Obtained Using the End-Tidal Method in Xenon-Enhanced CT", Shigeru Sase, Journal of Computer Assisted Tomography, 22 (5): 786–791, 1988}.

The correlation is as follows. That is, the velocity constant of the xenon gas concentration in the artery is expressed by a linear exponential function of the velocity constant of the xenon gas concentration in the end-tidal air by using a conversion constant.

SUMMARY OF THE INVENTION

This invention has been made taking the knowledge as described above into consideration, an object of which is to provide a method for determining a constant in a relational expression concerning the end-tidal air velocity constant and the arterial blood velocity constant, and a xenon CT apparatus which make it possible to correctly determine the cerebral blood flow rate by using the xenon gas concentration in the end-tidal air by utilizing the correlation between the xenon gas concentration of the blood flow in the artery and the xenon gas concentration in the end-tidal air.

According to the present invention, there is provided a method for determining a constant $\gamma$ in a relational expression:

$$Ka = \gamma \times (1 - \exp(-Ke/\gamma))$$

wherein Ke represents an end-tidal air velocity constant and Ka represents an arterial blood velocity constant in a xenon CT examination, the method comprising a step A of setting a region of interest on a xenon CT image; and a step B of determining the constant $\gamma$ with which a xenon distribution coefficient $\lambda$ most closely approaches a predetermined target value in the preset region of interest. As described above, it is possible to obtain a correct value of the constant $\gamma$ by determining the constant $\gamma$ by using the xenon distribution coefficient $\lambda$ as an index.

In the step B, the distribution coefficient $\lambda$ is calculated by varying the constant $\gamma$ within a desired range from 0.24 to 7.7 to determine the constant $\gamma$ with which the distribution coefficient $\lambda$ most closely approaches the target value. As described above, the range of the constant $\gamma$ to be considered is limited, and thus it is possible to shorten the processing period of time required to determine the constant $\gamma$.

In this case, it is also preferable that the desired range is a range from 0.3 to 2.5.

In the step B, the constant $\gamma$, with which a value of the distribution coefficient $\lambda$ most closely approaches the target value, is determined for each of predetermined picture elements included in the region of interest, and obtained values of the constant $\gamma$ are averaged to estimate an objective value of the constant $\gamma$. Accordingly, it is possible to determine the constant $\gamma$ more correctly.

Further, in the step A, the region of interest is set to a region including cerebral white matter, and in the step B, the target value is determined depending on a hematocrit value. Accordingly, it is possible to correctly determine the constant $\gamma$ in order to determine the cerebral blood flow rate.

According to the present invention, there is provided a xenon CT apparatus comprising a gas supply unit for supplying xenon gas to a specimen; a concentration-measuring unit for measuring a xenon gas concentration (hereinafter referred to as "expiration gas xenon gas concentration") in end-tidal air of the specimen; a main X-ray CT apparatus body for obtaining CT image data of an examination site in order to obtain a xenon gas concentration (hereinafter referred to as "examination site xenon gas concentration") of the examination site of the specimen; and a data processing unit for determining the examination site xenon gas concentration on the basis of the CT image data, and determining a blood flow rate of the examination site on the basis of the examination site xenon gas concentration and the expiration gas xenon gas concentration; wherein the data processing unit determines a xenon gas distribution coefficient $\lambda$ between the examination site and blood of the specimen on the basis of a conversion constant $\gamma$ for converting a velocity constant (hereinafter referred to as "expiration gas velocity constant") of the expiration gas xenon gas concentration into a velocity constant (hereinafter referred to as "arterial blood velocity constant") of a xenon gas concentration (hereinafter referred to as "arterial xenon gas concentration") of blood flow in artery, and it establishes, as a true value, the conversion constant γ with which the distribution coefficient λ most closely approaches a predetermined target value. As described above, it is possible to obtain a correct value of the conversion constant γ by determining the conversion constant γ by using the distribution coefficient λ as an index.

In this arrangement, the data processing unit includes a conversion constant-setting means for determining the conversion constant γ; and the conversion constant-setting means has an assumed value-setting means for setting an assumed value of the conversion constant γ and varying the assumed value.

The conversion constant-setting means includes a temporary velocity constant-setting means for determining a temporary calculated value of the arterial blood velocity constant from the expiration gas velocity constant on the basis of the assumed value of the conversion constant γ; a temporary distribution coefficient-calculating means for determining a temporary calculated value of the distribution coefficient λ from the temporary calculated value of the arterial blood velocity constant and the examination site xenon gas concentration; and a conversion constant-extracting means for extracting, as an extracted assumed value to be established as the true value, an assumed value of the conversion constant γ corresponding to one which most closely approaches the target value, of respective temporary calculated values of the distribution coefficient λ obtained on the basis of respective assumed values of the conversion constant γ.

The conversion constant-setting means includes a filtering means for determining, as a filtered value to be established as the true value, one in which the temporary calculated value of the distribution coefficient λ corresponding to the extracted assumed value is included in a predetermined filtration range, of the extracted assumed values.

The conversion constant-setting means includes an ROI data-extracting means for extracting examination site xenon gas concentrations respectively obtained on the basis of data corresponding to a plurality of predetermined picture elements, of data of respective picture elements included in the CT image data; and an average value-calculating means for determining, as the true value of the conversion constant γ, an average values of the filtered values obtained on the basis of the extracted examination site xenon gas concentrations respectively.

Accordingly, it is possible to determine the conversion constant γ more correctly.

The assumed value-setting means varies the assumed value of the conversion constant γ within a desired range from 0.24 to 7.7. As described above, the range of the assumed value to be considered is limited, and thus it is possible to shorten the processing period of time required to determine the conversion constant γ.

In this arrangement, it is also preferable that the desired range is a range from 0.3 to 2.5.

The conversion constant-setting means has a target value-calculating means for determining the target value; and the target value-calculating means determines the target value depending on a hematocrit value when the examination site is brain of the specimen, and a region of interest for determining the conversion constant γ is set to be a region including white matter of the brain. Accordingly, it is possible to correctly determine the conversion constant γ for determining the cerebral blood flow rate.

In this arrangement, a relational expression for determining the arterial blood velocity constant from the expiration gas velocity constant on the basis of the conversion constant γ is represented by:

$$Ka=\gamma \times (1-\exp(-Ke/\gamma))$$

wherein Ke represents the expiration gas velocity constant, and Ka represents the arterial blood velocity constant.

The xenon CT apparatus further comprises a display unit for displaying a distribution map of the blood flow rate and/or the conversion constant γ.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

An embodiment of the present invention will be explained below with reference to the drawings.

Figure 1:
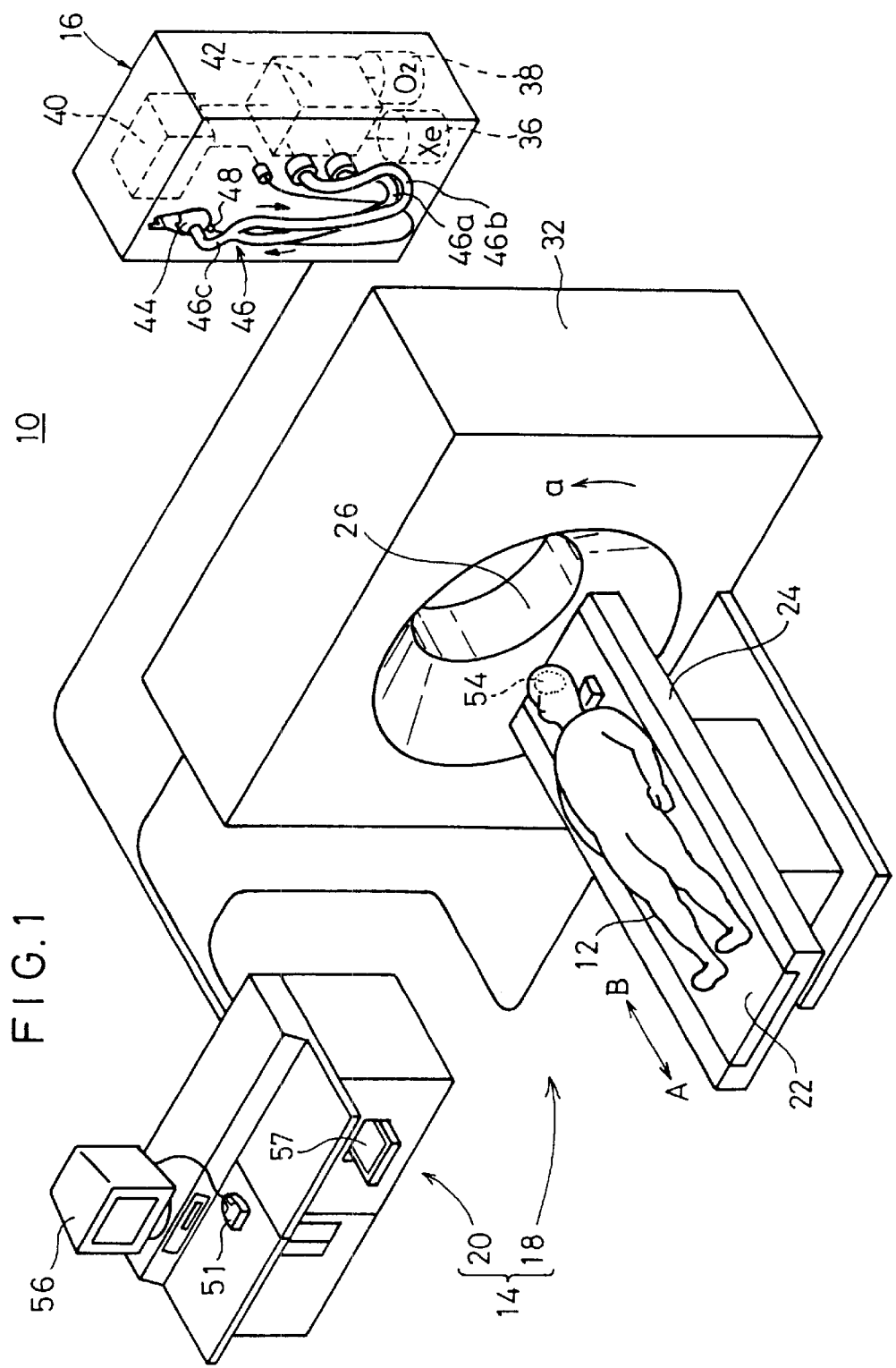
FIG. 1 shows a schematic view as viewed in perspective view illustrating an entire arrangement of an embodiment of the present invention.
Figure 2:
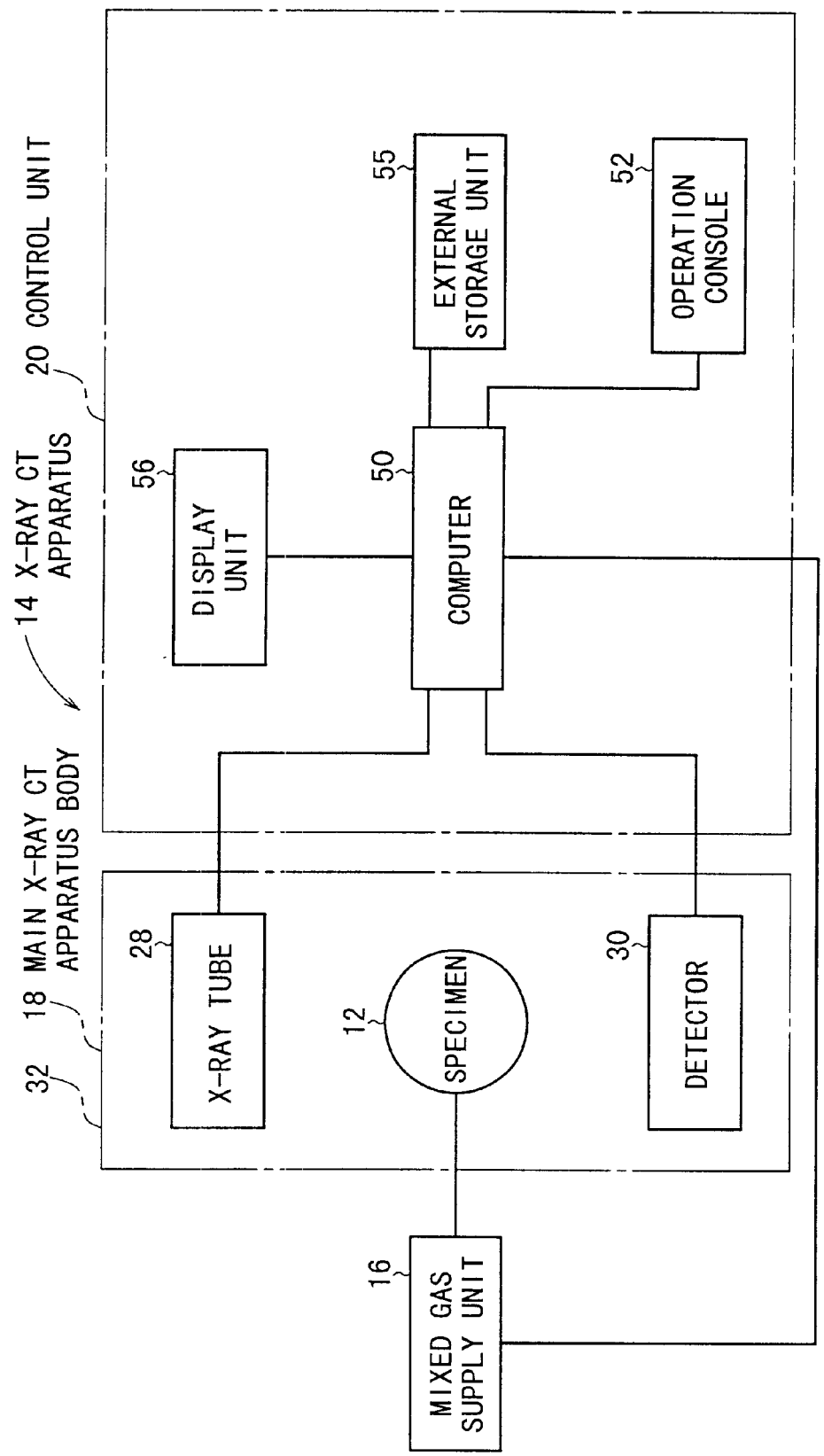
FIG. 2 shows a block diagram illustrating the arrangement of the embodiment of the present invention.

FIG. 1 shows an entire arrangement of a cerebral blood flow rate-measuring apparatus 10 according to this embodiment. FIG. 2 shows a block diagram of the cerebral blood flow rate-measuring apparatus shown in FIG. 1.

In FIGS. 1 and 2, the cerebral blood flow rate-measuring apparatus 10 is a xenon CT apparatus for performing the xenon CT examination for a specimen 12 such as human, and it basically comprises an X-ray CT apparatus 14 for obtaining a tomographic image (xenon CT image) of the specimen 12, and a mixed gas supply unit 16 for supplying mixed gas of xenon (Xe) and oxygen ($O_2$) to the specimen 12.

The X-ray CT apparatus 14 comprises a main X-ray CT apparatus body 18, and a control unit 20 for controlling the main X-ray CT apparatus body 18 and controlling the mixed gas supply unit 16. The control unit 20 also functions as a data processing unit for processing, for example, the image data obtained by the main X-ray CT apparatus body 18. It is also possible that the control unit 20 is constructed while being physically separated into a control unit for controlling the main X-ray CT apparatus body 18 and a control unit for controlling the mixed gas supply unit 16.

As shown in FIG. 1, the main X-ray CT apparatus body 18 includes a specimen-placing stand 24 with a movable table 22 for being moved in directions of arrows A and B while placing the specimen 12 thereon, the movable table 22 being arranged on the upper surface of the specimen-placing stand 24, and a gantry 32 formed with a cylindrical opening 26. The gantry 32 is arranged with an X-ray tube 28 (see FIG. 2) constructed to make swinging movement, for example, in a direction of an arrow "a" about the cylindrical opening 26, and a detector 30 (see FIG. 2) comprising a plurality of detectors arranged on the circumference around the opening 26.

As shown in FIG. 1, the mixed gas supply unit 16 has a xenon gas bomb 36, an oxygen gas bomb 38, a main inhalator body 42 for mixing the xenon gas and the oxygen gas under the control of an internal computer 40, and a conduit 46 with its one end connected to the main inhalator body 42 and with its other end connected to a breathing mask 44.

In this arrangement, the conduit 46 comprises an inspiration tube 46a, an expiration tube 46b, and a breathing mask conduit 46c. A xenon gas concentration-measuring sensor (concentration-measuring unit) 48 is attached to the breathing mask 44. A detection signal of the concentration-measuring sensor 48 is supplied to the computer 40. The xenon gas concentration in the expiration gas is calculated by the computer 40.

The computer 40, which controls the entire operation of the mixed gas supply unit 16, is electrically connected to the control unit 20 to make mutual communication with each other.

As shown in FIG. 2, the control unit 20 of the X-ray CT apparatus 14 has a computer 50 which functions as a control unit and a processing unit. The computer 50 controls the operation of the main X-ray CT apparatus body 18 and the mixed gas supply unit 16. The computer 50 processes the picture element data for constructing the tomographic image of the brain 54 as an examination site of the specimen 12, detected by the detector 30 in the gantry 32 to prepare, for example, the tomographic image.

Those further connected with the computer 50 include an operation console 52 having a mouse 51 (see FIG. 1) and a keyboard, an external storage unit 55 such as a magneto-optical disk unit and a magnetic disk unit, and a display unit 56 such as color CRT.

In the cerebral blood flow rate-measuring apparatus 10 of the embodiment shown in FIGS. 1 and 2, the operation console 52 is practically operated as follows. That is, a concerning display on the screen is clicked by a mouse pointer which is displayed on the screen of the display unit 56 and which is operated by the mouse 51 to instruct the execution of the process indicated by the concerning display.

The tomographic image (so-called CT image) of the brain 54 or the like, which is depicted by the CT picture element data obtained by the main X-ray CT apparatus body 18 by the aid of the processing effected by the computer 50 as described later on, is displayed in color or monochrome on the display unit 56. Further, the image of the cerebral blood flow rate is displayed on the display unit 56. The image, which is displayed on the screen of the display unit 56, can be printed out by means of a printer contained in the control unit 20 to output a color or monochrome hard copy 57 (see FIG. 1).

Next, the operation of this embodiment will be explained on the basis of a flow chart shown in FIG. 3. The control entity of the flow chart is the computer 50.

Figure 4:
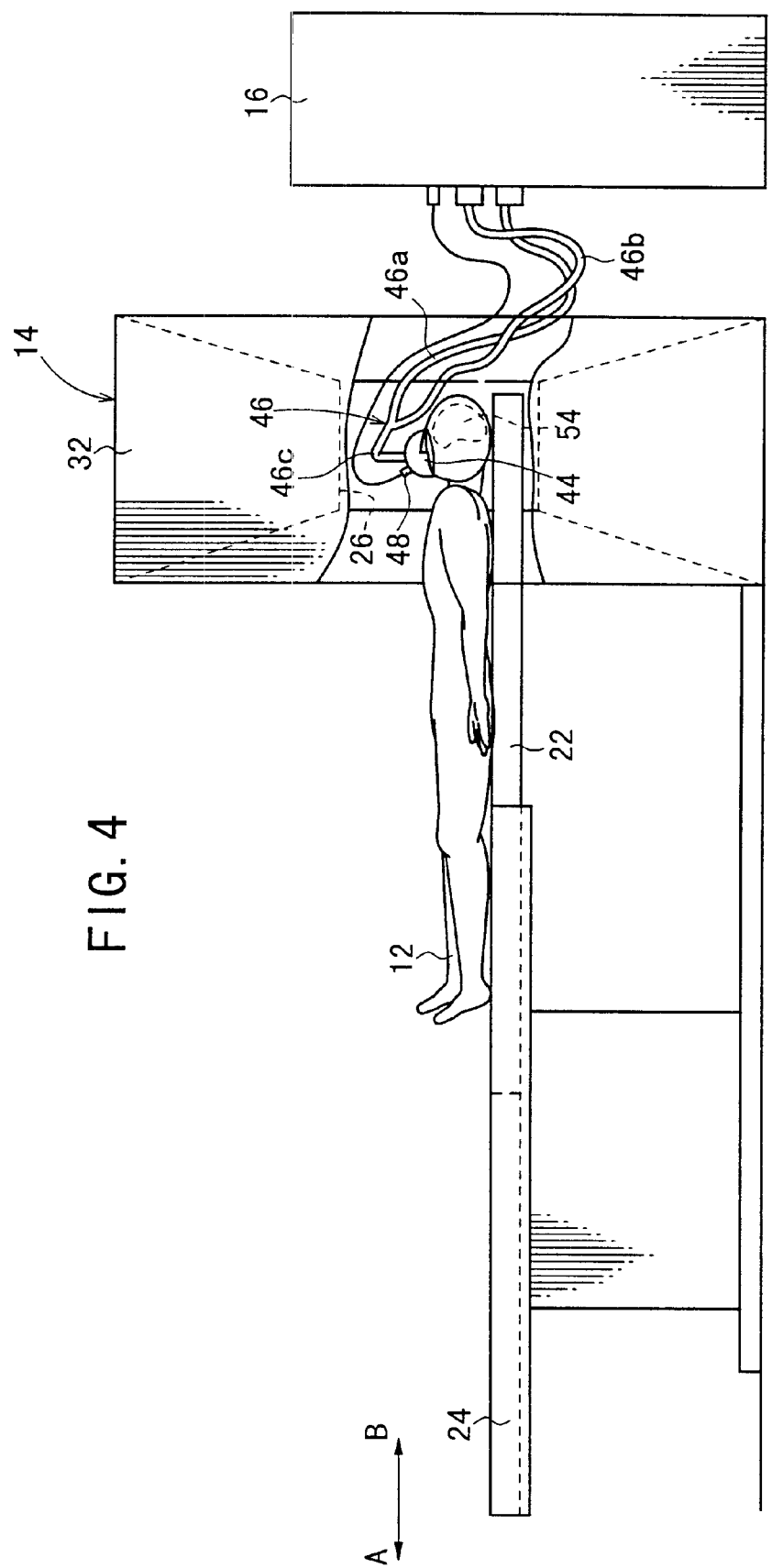
FIG. 4 shows a schematic view as viewed in side view illustrating a state in which brain of a patient, which is a specimen supplied with xenon gas, is photographed by using an X-ray CT apparatus.

At first, in the step Si, an operator such as a medical doctor operates the operation console 52 to move the movable table 22 in the direction of the arrow B in a state in which the specimen 12 is placed on the specimen-placing stand 24 as shown in FIG. 4. The movable table 22 is stopped at a position at which the tomographic image of the brain 54 of the specimen 12 can be photographed.

Subsequently, in the step S2, as shown in FIG. 4, the breathing mask 44 is attached so that the mouth and the nose of the specimen 12 are covered therewith.

In the step S3, the operation console 52 is operated in the state shown in FIG. 4 in which the measurement can be performed. Accordingly, a measurement start command is fed from the computer 50 of the control unit 20 to the computer 40 of the mixed gas supply unit 16 and the main X-ray CT apparatus body 18 respectively.

At this time, at first, in the step S4, the tomographic image of the brain 54, i.e., the so-called baseline CT image is photographed by the main X-ray CT apparatus body 18, and the image is incorporated into the external storage unit 55.

Subsequently, the xenon gas and the oxygen gas, which are fed from the xenon gas bomb 36 and the oxygen gas bomb 38, are mixed in a ratio of the xenon gas: 30% and the oxygen gas: 70% by the main inhalator body 42 under the control of the computer 40 of the mixed gas supply unit 16. The mixed gas is supplied to the lungs of the specimen 12 via the inspiration tube 46a, the breathing mask conduit 46c, and the breathing mask 44. The expiration gas, which is discharged from the lungs of the specimen 12, is returned to the main inhalator body 42 via the breathing mask 44, the breathing mask conduit 46c, and the expiration tube 46b.

At this time, in the step S5, the mixed gas supply unit 16 is controlled by the computer 40 so that the concentration of the xenon gas in the mixed gas has a predetermined value (in this case, 30%) to start the measurement, from the point of time at which the supply of the mixed gas to the specimen 12 is started. Thus, the inhalation process, i.e., the so-called Wash-in is started.

For example, an apparatus disclosed in Japanese Patent Publication No. 3-33326 by the present applicant can be used as the mixed gas supply unit 16. The concentration of the xenon gas in the expiration gas is measured, for example, at intervals of 40 ms from the point of time of the start of the measurement.

In the step S6, the process is performed, for example, for the changeover to the saturation judgement and the washing process, i.e., the so-called Wash-out process as described later on, from the point of time of the start of the inspiration of the mixed gas with respect to the specimen 12, during which the X-ray is radiated to the specimen 12 at intervals of about 60 s from the X-ray tube 28 in the gantry 32. The X-ray, which has passes through the specimen 12, is detected by the detector 30. Accordingly, the tomographic image of the brain 54 is photographed at intervals of about 60 s, and it is incorporated as the CT picture element data into the computer 50.

Subsequently, in the step S7, the CT value (i.e., the Hounsfield unit [HU]) is extracted from the CT picture element data for each of the picture elements. The xenon gas concentration in the cerebral tissue is calculated for each of the picture elements on the basis of the CT value. In this embodiment, the size of the picture element is about 0.5 mm square. However, the size may be changed into an appropriate size.

The xenon gas concentration of each of the picture elements is calculated by using the moving average method. That is, the xenon gas concentration is determined for each of the picture elements from the measurement region which is composed of a plurality of picture elements (for example, 7×7 individuals, 9×9 individuals, or 11×11 individuals, preferably 9×9 individuals). Further, an average value of the xenon gas concentrations over the entire region is calculated, for example, as a xenon gas concentration of the picture element which is located at the center of the measurement region. The xenon gas concentration of each of the picture elements is calculated while moving the measurement region by a width of a unit of one picture element or a unit of a plurality of picture elements (for example, unit of nine picture elements as a measurement region unit).

In order that the invention is understood easily, it is conveniently assumed that the phrase "for (of) each picture element" referred to in the following description has the same meaning as the phrase "for (of) each tissue or for (of) each of respective tissues" for constructing the brain 54.

Figure 5:
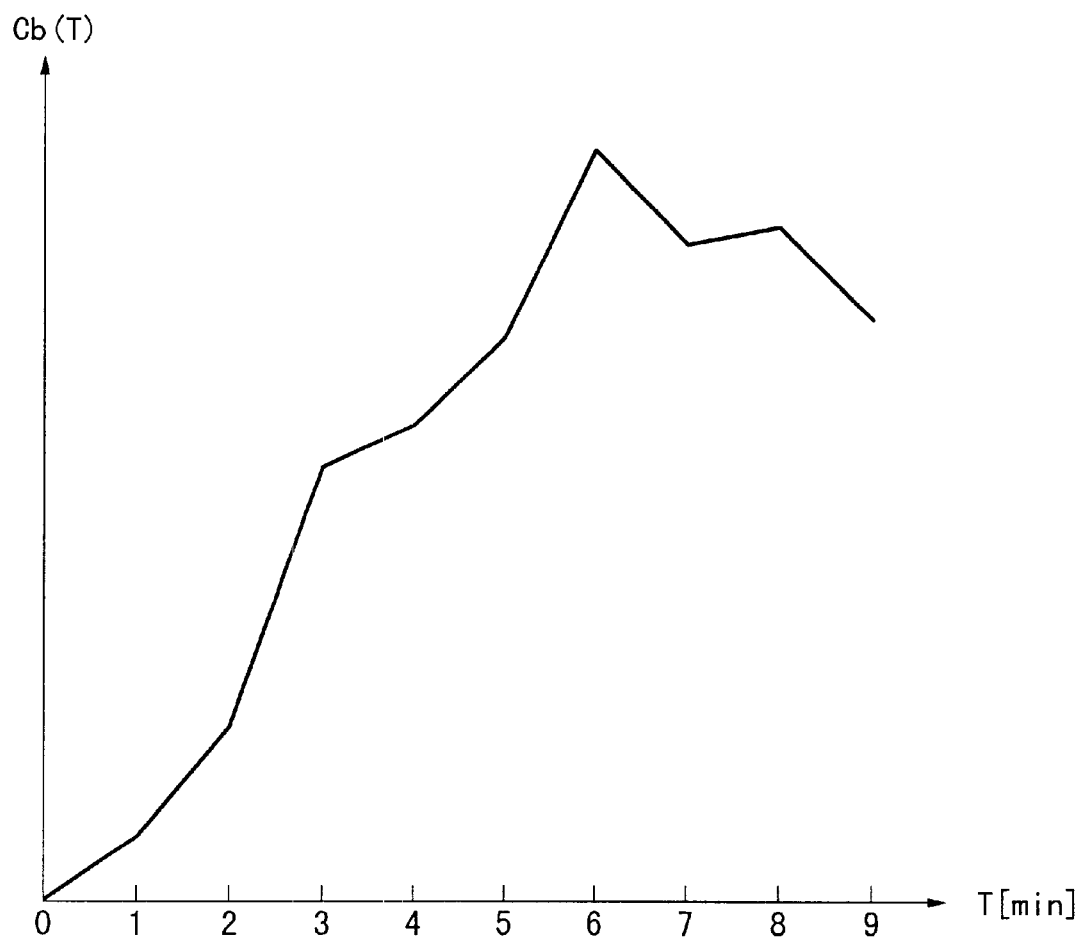
FIG. 5 shows a characteristic curve illustrating the change of the cerebral xenon gas concentration.

As described above, as shown in FIG. 5, it is possible to obtain the xenon gas concentration of each of the tissues of the brain 54 (cerebral xenon gas concentration) Cb(T) [mg/ml] {T represents the point of time of measurement [s], which has values at intervals of about 60 s (1 min) such as T=0, 62, 123, 183, 243, 303, 363, 424, 484, 544, ... } as the xenon gas concentration of the examination site of the specimen 12.

Subsequently, in the step S8, if the rate of increase of the cerebral xenon gas concentration Cb(T) is smaller than a preset predetermined value, it is judged that the saturated state is given. In the following step S9, it is judged whether or not the Washing-out process is completed. After that, in the step S10, the supply of the mixed gas is stopped to perform the so-called Wash-out so that the ordinary air is fed in place of the mixed gas.

Further, the process in the step S6 is performed at intervals of about 1 min (60 s), and the process in the step S7 is performed at intervals of 40 ms. On the other hand, the process in the step S6 is performed at intervals of about 1 min, and the process in the step S7 is performed at intervals of 40 ms in the same manner as described above, until it is confirmed in the step S11 that the cerebral xenon gas concentration Cb(T) is not more than a predetermined value, after completing the Washing-out process (after the judgement in the step S9 is affirmative). If the cerebral xenon gas concentration Cb(T) is not more than the predetermined value (step S11: YES), the cerebral blood flow rate is calculated in the step S12 as explained below, on the basis of the concentration data of the expiration gas determined by the xenon gas concentration-measuring sensor 48 and the cerebral xenon gas concentration Cb(T) of the brain 54.

In the following step S13, various displays are made on the display unit 56, for example, on the basis of the calculation result as described later on.

Next, the process in the step S12 for calculating the cerebral blood flow rate for each tissue of the brain 54 will be explained in detail below.

At first, explanation will be made for the algorithm for calculating the cerebral blood flow rate. In the following description, Ce(t) [mg/ml] represents the xenon gas concentration in the end-tidal air (expiration gas xenon gas concentration) at an arbitrary point of time of measurement t [s], Ca(t) [mg/ml] represents the xenon gas concentration of the blood flow in the artery (in this case, the artery other than the pulmonary artery, for example, the carotid artery), i.e., the xenon gas concentration (arterial xenon gas concentration) of the arterial blood flow flowing into the brain 54, Ka [min$^{-1}$] represents the velocity constant (arterial blood velocity constant) of the arterial xenon gas concentration Ca(t), Ke [min$^{-1}$] represents the velocity constant (end-tidal air velocity constant) of the expiration gas xenon gas concentration Ce(t), f [ml/g/min] represents the cerebral blood flow rate, and λ represents the brain/blood distribution coefficient (the xenon distribution coefficient between the brain 54 and the blood of the specimen 12).

The following expression (1) is the Kety-Schmidt expression which is used to determine the cerebral blood flow rate f in this embodiment.

$$Cb(T)=f\times\int_0^T Ca(t)\times\exp(-f\times(T-t)/\lambda)dt \quad (1)$$

wherein the variable range of the definite integral on the right side is [0, T].

The cerebral xenon gas concentration Cb(T) on the left side in the expression (1) is determined on the basis of the CT value included in the CT image data obtained by the X-ray CT apparatus 14 at the point of time of measurement T.

The solution of the definite integral on the right side in the expression (1) is determined in accordance with the following procedure.

Figure 6:
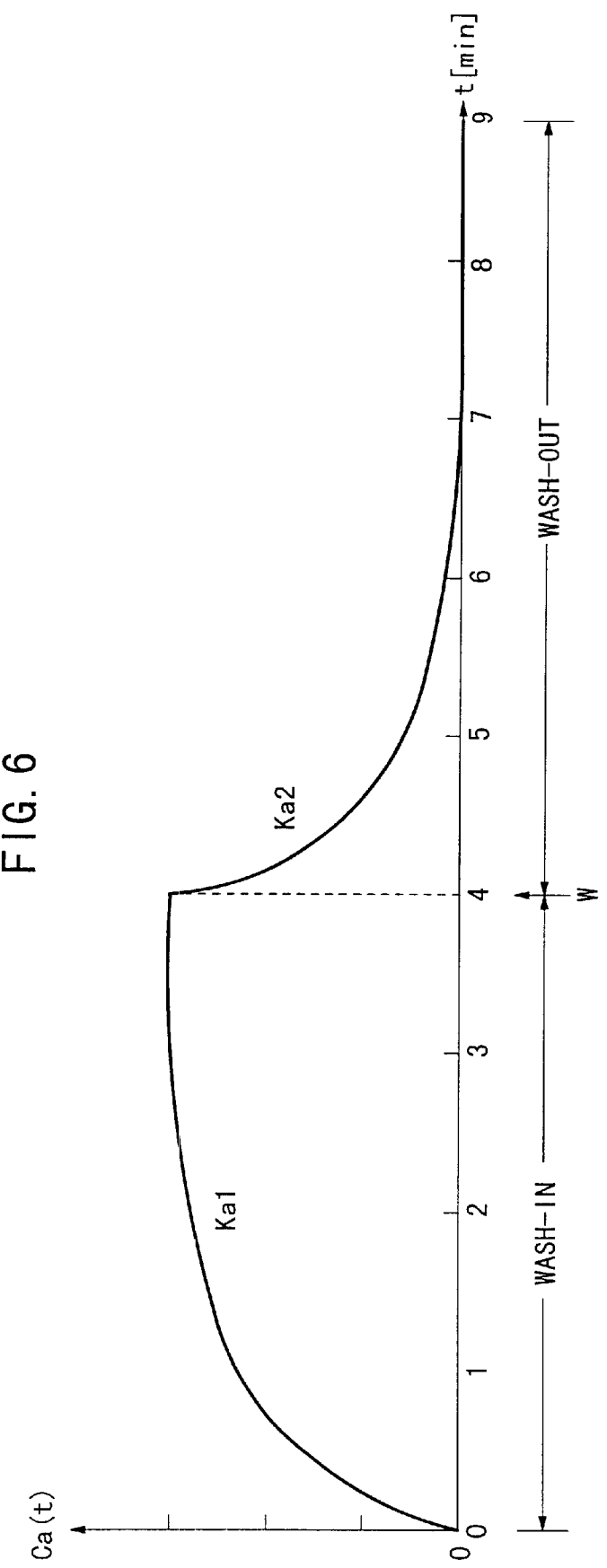
FIG. 6 shows a characteristic curve illustrating the change of the arterial xenon gas concentration.

FIG. 6 shows a characteristic of the arterial xenon gas concentration Ca(t) obtained, for example, on the basis of the experimental data. In FIG. 6, the period of the point of time t=0 to w is the period of the inhalation process (Wash-in), and the period of the point of time t=w to 9 is the period of the washing process (Wash-out).

It is known that the characteristic of the time-dependent change (transition with respect to the point of time of measurement t) of the arterial xenon gas concentration Ca(t) is approximated, for example, by the linear exponential function of the following expression (2) in the Wash-in period in accordance with the least square method, and it is approximated, for example, by the linear exponential function of the following expression (3) in the Wash-out period.

$$Ca(t)=Aa \times (1-\exp(-Kai \times t)) \quad (2)$$

$$Ca(t)=Caw \times \exp(-Kao \times (t-w)) \quad (3)$$

In the expressions, Aa represents a predetermined constant, and Caw represents the value of the arterial xenon gas concentration Ca(t) at the point of time t=w. Kai represents the arterial blood velocity constant Ka in the Wash-in period, and Kao represents the arterial blood velocity constant Ka in the Wash-out period.

The arterial blood velocity constants Kai, Kao in the expressions (2) and (3) can be determined from expiration gas velocity constants Kei, Keo of the expiration gas xenon gas concentration Ce(t) (Kei represents the expiration gas velocity constant Ke in the Wash-in period, and Keo represents the expiration gas velocity constant Ke in the Wash-out period). Especially, in this embodiment, the arterial blood velocity constants Kai, Kao are determined according to the relational expressions {the following expressions (4) and (5)} concerning the arterial blood velocity constants Kai, Kao and the expiration gas velocity constants Kei, Keo clarified by the inventors of the present application.

$$Kai=\gamma \times (1-\exp(-Kei/\gamma)) \quad (4)$$

$$Kao=\gamma \times (1-\exp(-Keo/\gamma)) \quad (5)$$

In the expressions, $\gamma$ represents the Ke/Ka conversion constant, which is a parameter to indicate the gas exchange ability in the lungs.

The expiration gas velocity constants Kei, Keo in the expressions (4) and (5) are determined, for example, from the following expressions (6) and (7) respectively obtained by the least square method from the data of the expiration gas xenon gas concentration Ce(t) obtained by the concentration-measuring sensor 48 {having the characteristic of the time-dependent change similar to the arterial xenon gas concentration Ca(t) shown in FIG. 6}.

$$Ce(t)=Ae \times (1-\exp(-Kei \times t)) \quad (6)$$

$$Ce(t)=Cew \times \exp(-Keo \times (t-w)) \quad (7)$$

In the expressions, Ae represents a predetermined constant, and Cew represents the value of the expiration xenon gas concentration Ce(t) at the point of time t=w.

That is, the arterial blood velocity constants Kai, Kao can be determined on the basis of the expiration gas xenon gas concentration Ce(t) as the actually measured value, by specifying the Ke/Ka conversion constant $\gamma$.

Explanation will now be made for the procedure for specifying the range which can be possessed by the value of the Ke/Ka conversion constant $\gamma$.

Figure 7:
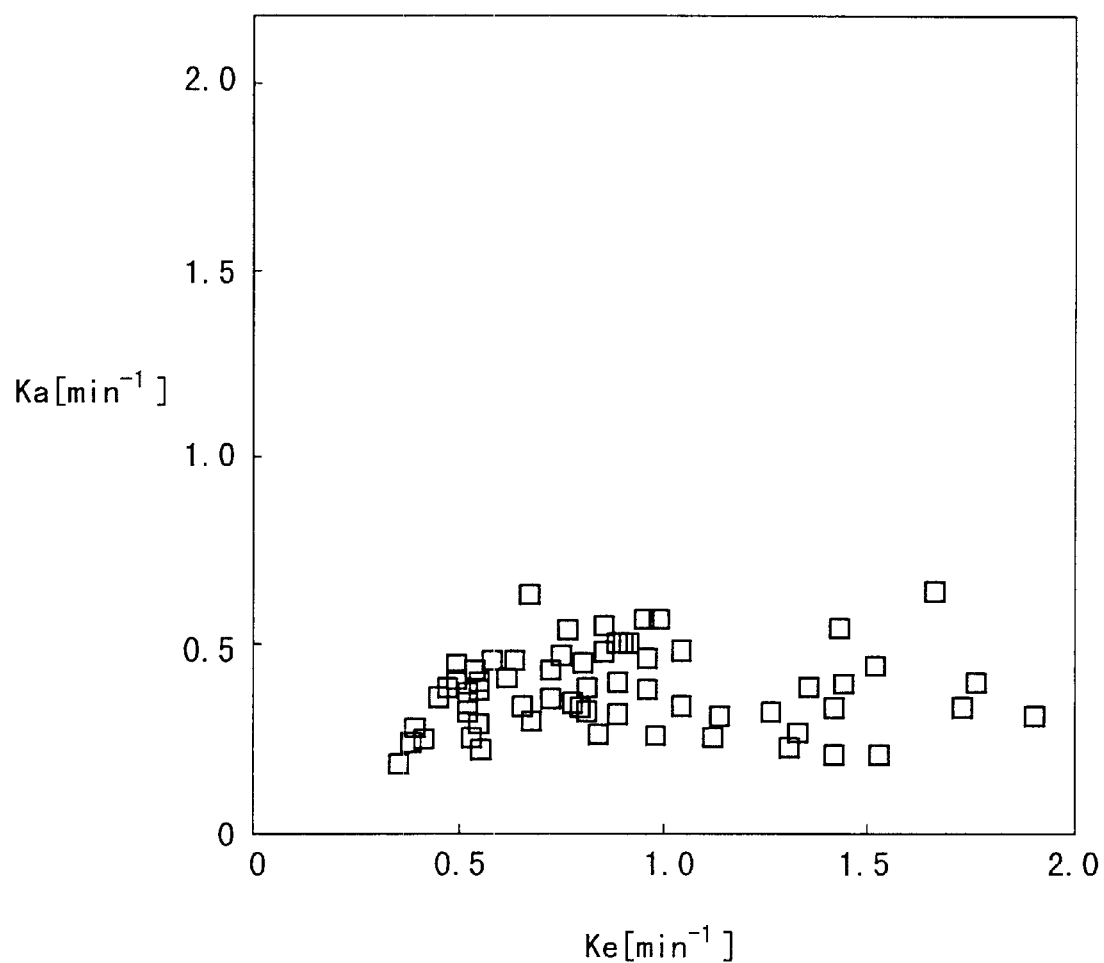
FIG. 7 shows a graph illustrating a relationship between the expiration gas velocity constant and the arterial blood velocity constant.

FIG. 7 shows a graph depicting the experimental data (indicated by symbols "□") for recording the relationship between the expiration gas velocity constant Ke and the arterial blood velocity constant Ka disclosed by Shimoda et al. (see "Discrepancy of xenon concentrations between end-tidal and blood collection methods in xenon-enhanced computed tomographic measurement of cerebral blood flow", M. Shimoda, et al., Neuroradiology, 35: 66–68, 1992).

Figure 8:
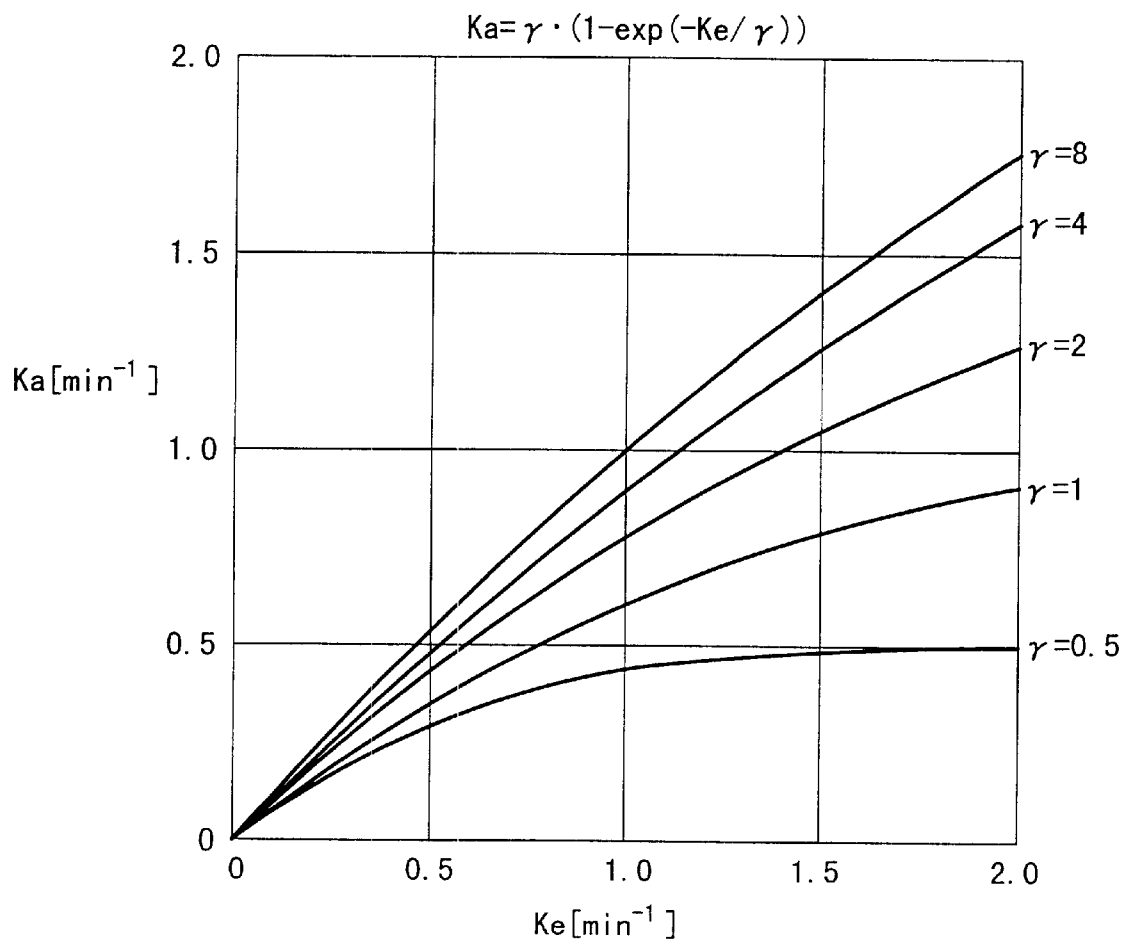
FIG. 8 shows a graph illustrating characteristics of the relational expression of the expiration gas velocity constant and the arterial blood velocity constant.

FIG. 8 shows a graph depicting the characteristic of the expressions (4) or (5) (in this case, it is assumed that Ka=Kai or Ka=Kao is given) for each of cases of $\gamma$=0.5, 1, 2, 4, 8.

Figure 9:
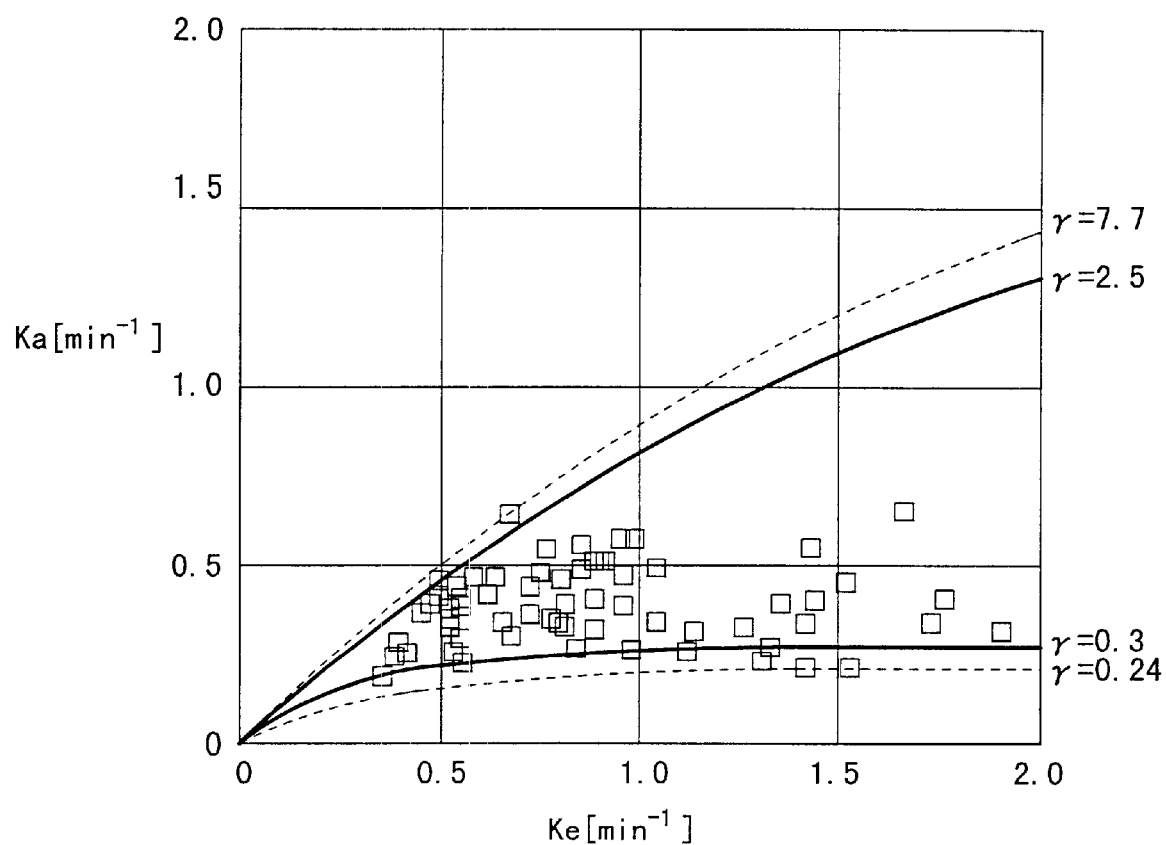
FIG. 9 shows a graph obtained by superimposing the graph shown in FIG. 8 on the graph shown in FIG. 7.

FIG. 9 shows a graph in which the graph shown in FIG. 8 is superimposed on the graph shown in FIG. 7 {in this case, $\gamma$=0.3, 2.5 (indicated by solid lines), and 0.24, 7.7 (indicated by broken lines)}.

As shown in FIG. 9, all of the positions of the symbols "□" are included in a region interposed between the curves which represent the characteristics of the expressions (4) and (5) in the case of $\gamma$=0.24 and 7.7 indicated by broken lines. Especially, a large number of the positions of the symbols "□" are included in a region interposed between the curves which represent the characteristics in the case of $\gamma$=0.3 and 2.5 indicated by solid lines.

That is, all of the Ke/Ka conversion constants $\gamma$, which are obtained on the basis of the relationship between the expiration gas velocity constant Ke and the arterial blood velocity constant Ke as shown in FIG. 7, are included in the range of $\gamma$=0.24 to 7.7, and most of them are included in the range of $\gamma$=0.3 to 2.5. Accordingly, the range of the value of the Ke/Ka conversion constant $\gamma$ in the expressions (4) and (5) can be limited to be the range of $\gamma$=0.24 to 7.7, especially the range of $\gamma$=0.3 to 2.5.

The range, in which the assumed value $\gamma\alpha$ of the Ke/Ka conversion constant $\gamma$ is to be varied as described later on, can be restricted by specifying the range in which the value of the Ke/Ka conversion constant $\gamma$ is allowed to vary. Therefore, it is possible to shorten the processing time.

The range of the value of the Ke/Ka conversion constant $\gamma$ can be changed, for example, on the basis of another experimental data which supplements the experimental data shown in FIG. 7.

Next, explanation will be made for the procedure for specifying the value of the Ke/Ka conversion constant $\gamma$.

This embodiment is principally characterized in that the Ke/Ka conversion constant $\gamma$ is specified by using the LGC method (Lambda-Guided Calculation Method) described below, i.e., the technique for determining the Ke/Ka conversion constant $\gamma$ by using the brain/blood distribution coefficient $\lambda$ in the expression (1) as an index.

In the LGC method, at first, an arbitrary value of the Ke/Ka conversion constant $\gamma$, which is included in a desired range (for example, a range of $\gamma$=0.3 to 2.5), is designated as the assumed value $\gamma\alpha$. The arterial xenon gas concentration Ca(t) is determined on the basis of the expressions (2) to (5) from the assumed value $\gamma\alpha$ and the expiration gas xenon gas concentration Ce(t) as the measured value. The calculation processing in the expression (1) is performed with the arterial xenon gas concentration Ca(t) and the cerebral xenon gas concentration Cb(T) as the measured value at each point of time of measurement T to thereby determine the temporary calculated value $\lambda\gamma$ of the brain/blood conversion constant $\lambda$ corresponding to the assumed value $\gamma\alpha$.

Similarly, the temporary calculated values $\lambda\alpha$ corresponding to the assumed values $\gamma\alpha$ are determined respectively while varying the assumed value $\gamma\alpha$ within the desired range. The temporary calculated value $\lambda\alpha$ is compared with a target value $\lambda\tau$ as an index as described later on, and thus the temporary calculated value $\lambda\alpha$, which is closest to the target value $\lambda\tau$, is extracted. The assumed value $\gamma\alpha$, which corresponds to the temporary calculated value $\lambda\alpha$ (i.e., the assumed value $\gamma\alpha$ with which the temporary calculated value $\lambda\alpha$ most closely approaches the target value $\lambda\tau$), is established as the true Ke/Ka conversion constant $\gamma$.

The reason why the Ke/Ka conversion constant $\gamma$ can be determined on the basis of the target value $\lambda\tau$ of the brain/blood distribution coefficient $\lambda$ as the index as described above is that the following correlation is provided between the brain/blood distribution coefficient $\lambda$ and the arterial blood velocity constants Kai, Kao especially at the white matter portion of the brain 54.

Figure 10:
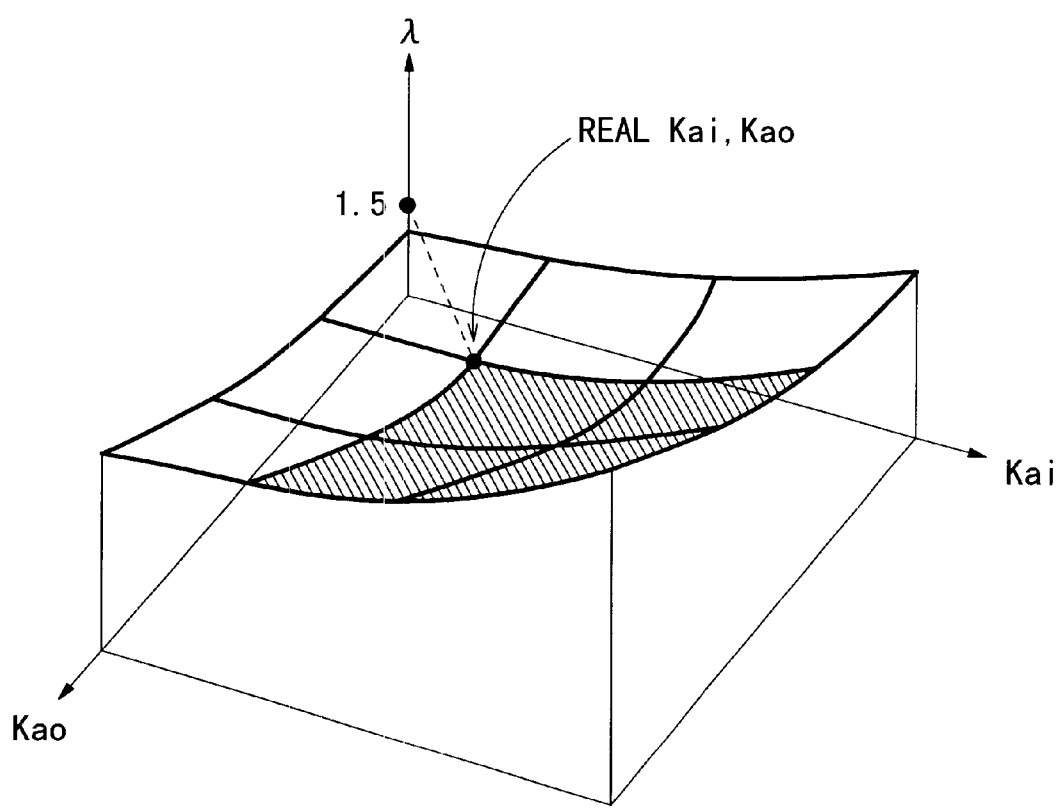
FIG. 10 shows a graph illustrating a relationship between the brain/blood distribution coefficient and the arterial blood velocity constant.

FIG. 10 shows a graph illustrating the relationship between the brain/blood distribution coefficient λ and the arterial blood velocity constants Kai, Kao. It is known that when the arterial blood velocity constants Kai, Kao have the correct values (REAL values), the value of the brain/blood distribution coefficient λ at the white matter portion is about 1.5. On the other hand, if the arterial blood velocity constants Kai, Kao are evaluated to be too large, or if they are evaluated to be too small, then the value of the brain/blood distribution coefficient λ is separated from 1.5.

Therefore, the values of the arterial blood velocity constants Kai, Kao, with which the temporary calculated value λα of the brain/blood distribution coefficient λ is about 1.5, are regarded as the correct values. Further, it can be judged that the assumed value γα, which makes it possible to obtain the correct values of the arterial blood velocity constants Kai, Kao from the expression (4) or (5) described above, is the true Ke/Ka conversion constant γ.

The correct value of the brain/blood distribution coefficient λ at the white matter portion can be determined by calculation as described later on.

Next, explanation will be made for the means (data processing means) of the computer 40 for performing the process in the step S12 shown in FIG. 3 (process for calculating the cerebral blood flow rate).

Figure 11:
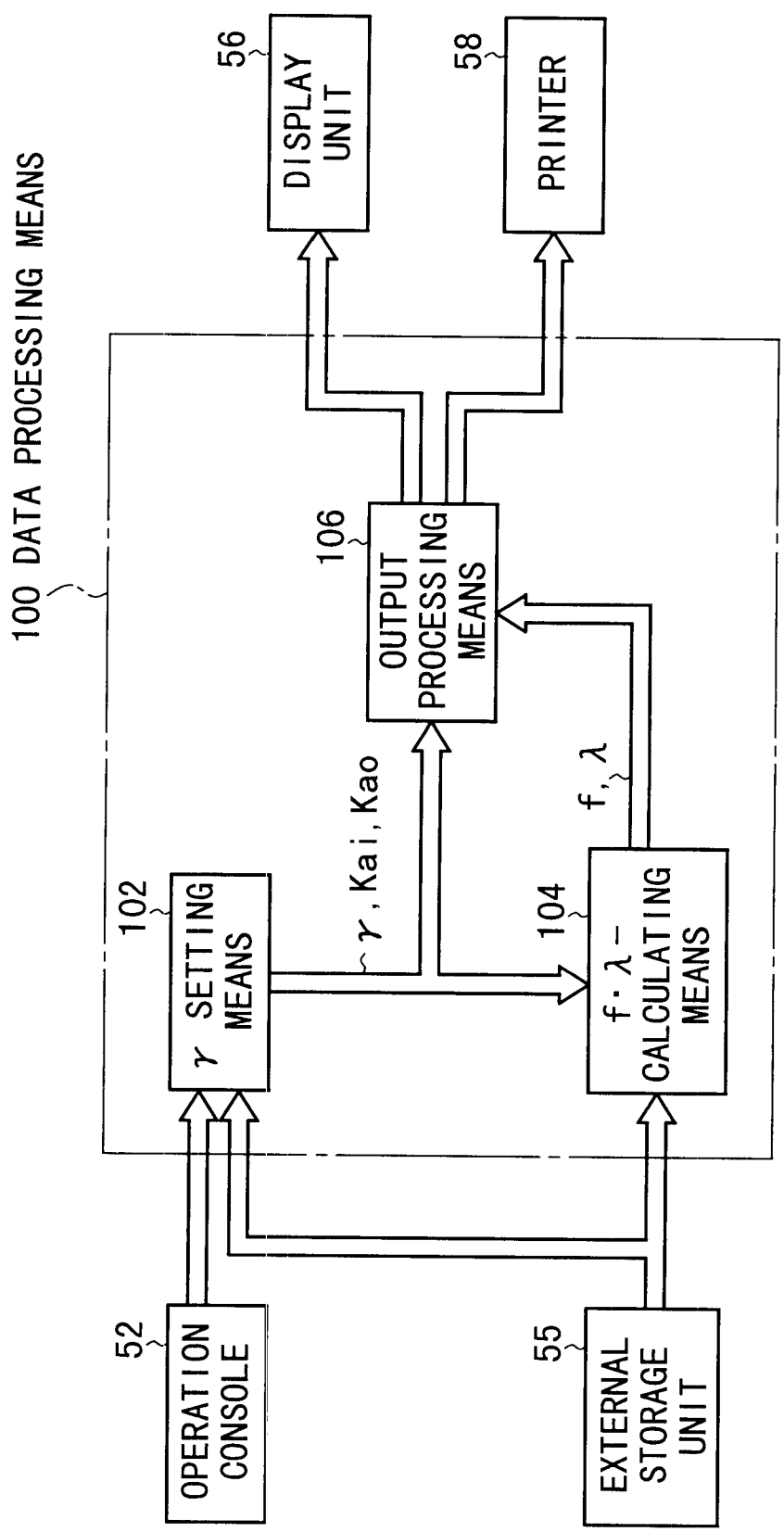
FIG. 11 shows a functional block diagram illustrating a schematic arrangement of a data processing means of a computer.

FIG. 11 shows a functional block diagram illustrating a schematic arrangement of the data processing means 100 of the computer 40.

The data processing means 100 comprises a γ-setting means (conversion constant-setting means) 102 for determining the true Ke/Ka conversion constant γ and determining the arterial blood velocity constants Kai, Kao on the basis of the Ke/Ka conversion constant γ, an f·λ-calculating means 104 for determining the cerebral blood flow rate f and the brain/blood distribution coefficient λ on the basis of the arterial blood velocity constants Kai, Kao determined by the γ-setting means 102, and an output processing means 106 for preparing, for example, output image data on the basis of, for example, the Ke/Ka conversion constant γ, the cerebral blood flow rate f, and the brain/blood distribution coefficient λ.

Figure 12:
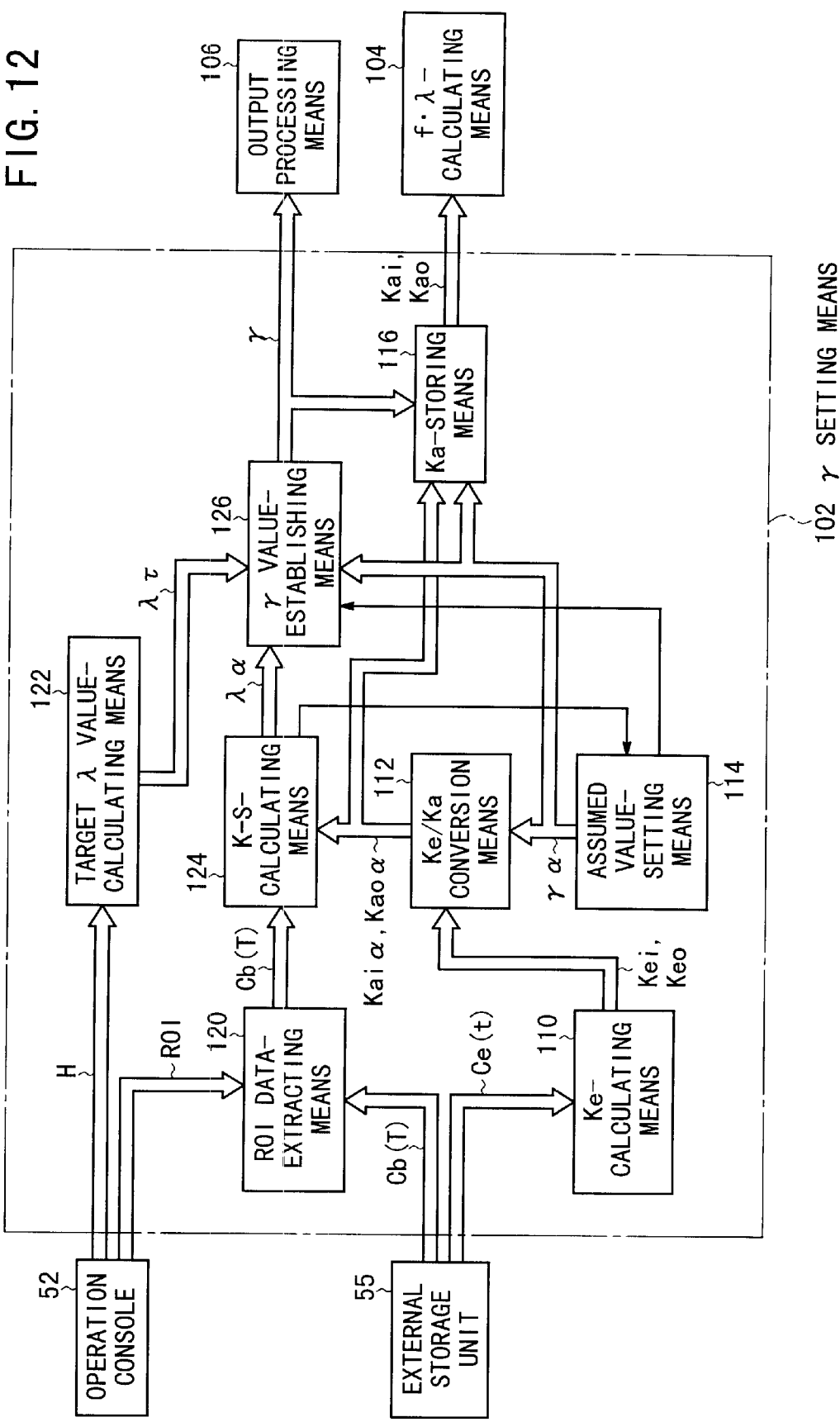
FIG. 12 shows a functional block diagram illustrating a schematic arrangement of a γ-setting means of the data processing means shown in FIG. 11.

FIG. 12 shows a functional block diagram illustrating a schematic arrangement of the γ-setting means 102. The γ-setting means 102 comprises a Ke-calculating means 110, a Ke/Ka conversion means (temporary velocity constant-setting means) 112, an assumed value-setting means 114, and a Ka-storing means 116.

The Ke-calculating means 110 firstly reads, from the external storage unit 55, the expiration gas xenon gas concentration Ce(t) which is detected at intervals of predetermined period of time (40 ms) by the concentration-measuring sensor 48 of the mixed gas supply unit 16 (see FIG. 1) and which is stored in the external storage unit 55. The approximate expressions referred to as the expressions (6) and (7) (especially the expiration gas velocity constants Kei, Keo in these expressions) are determined from the expiration gas xenon gas concentration Ce(t) in accordance with the least square method.

The Ke/Ka conversion means 112 performs the calculation processing based on the expressions (4) and (5) on the basis of the expiration gas velocity constants Kei, Keo from the Ke-calculating means 110 and the assumed value γα of the Ke/Ka conversion constant γ from the assumed value-setting means 114 to thereby determine the temporary calculated values Kaiα, Kaoα of the arterial blood velocity constants Kai, Kao.

In this process, the assumed value-setting means 114 increases the assumed value γα, for example, from 0.3 to 2.5, for example, by 0.01 in accordance with a control signal from the K-S-calculating means described later on.

The assumed value γα from the assumed value-setting means 114 and the temporary calculated values Kaiα, Kaoα from the Ke/Ka conversion means 112 corresponding thereto are accumulated in the Ka-storing means 116 respectively.

The γ-setting means 102 includes an ROI data-extracting means 120, a target λ value (target value)-calculating means 122, a K-S-calculating means (temporary distribution coefficient-calculating means) 124, and a γ value-establishing means 126.

Figure 13:
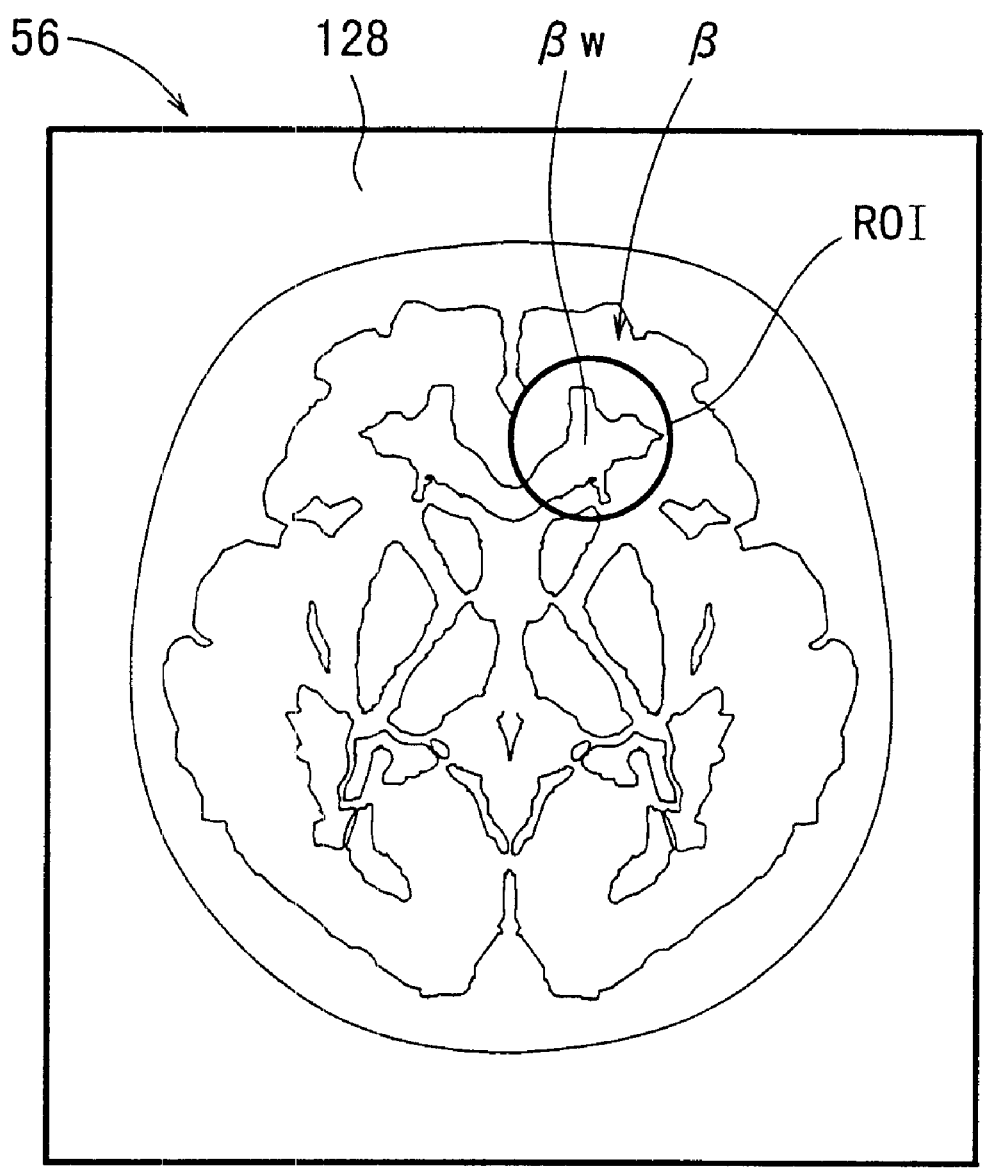
FIG. 13 shows a region of interest set on a tomographic image of brain.

FIG. 13 shows a region of interest ROI set on a tomographic image β of the brain 54.

The ROI data-extracting means 120 shown in FIG. 12 specifies picture elements included in the region of interest ROI (see the region indicated by a circle in FIG. 13) set by the operator by the aid of the operation console 52 as shown in FIG. 13.

In this case, the operator performs the operation for setting the region of interest ROI in accordance with the operation in which a specified region (preferably a region to include the white matter portion βw of the frontal lobe containing a large amount of white matter) is surrounded by the circle, concerning the tomographic image β of the brain 54 (especially, an image of a tomographic plane on which the cerebral basal ganglia appears) displayed on the screen 128 of the display unit 56.

It is possible to prevent the subjectivity of the operator from being reflected to the setting operation for the region of interest ROI, by setting the region of interest ROI to surround the white matter portion βw of the frontal lobe as described above. Alternatively, the region of interest ROI may be automatically set by detecting the position of the white matter portion βw of the frontal lobe by means of the image processing.

As shown in FIG. 12, the ROI data-extracting means 120 extracts one corresponding to the picture element included in the region of interest ROI, from the cerebral xenon gas concentrations Cb(T) which are detected at respective points of time of measurement T at the predetermined time intervals (about 60 s) by the detector 30 (see FIG. 2) of the main X-ray CT apparatus body 18 and which are stored in the external storage unit 55.

In this case, it is assumed that the cerebral xenon gas concentrations Cb(T) are previously calculated by the control unit 20 on the basis of the CT image data from the main X-ray CT apparatus body 18 as shown in FIG. 2, and they are stored in the external storage unit 55. When the cerebral xenon gas concentration Cb(T) is determined, the moving average processing is applied for the picture element range, for example, of 9×9 individuals suitable to remove any noise as described above.

As shown in FIG. 12, the K-S-calculating means 124 performs the calculation processing based on the use of the expressions (1) to (3), on the basis of the cerebral xenon gas concentration Cb(T) (including the information on the point of time of measurement T as well) from the ROI data-extracting means 120, and the temporary calculated values Kaiα, Kaoα of the arterial blood velocity constants Kai, Kao from the Ke/Ka conversion means 112. The calculation is performed while substituting Kai, Kao in the expressions (2) and (3) with Kaiα, Kaoα.

The temporary calculated value λα of the brain/blood distribution coefficient λ, which is obtained by the calculation processing as described above, is supplied to the γ value-establishing means 126 together with the assumed value γα from the assumed value-setting means 114 corresponding thereto. In the calculation processing, the cerebral blood flow rate f is actually determined as well. However, the cerebral blood flow rate f is not considered in the γ value-establishing means 126.

When the calculation processing for the temporary calculated value λα based on one assumed value γα is completed, the K-S-calculating means 124 outputs, to the assumed value-setting means 114, the control signal to output the next assumed value γα (assumed value γα with a value increased by 0.01).

The target value λτ of the brain/blood distribution coefficient λ from the target λ value-calculating means 122 is also supplied to the γ value-establishing means 126 together with the temporary calculated value λα from the K-S-calculating means 124.

The target value λτ is a brain/blood distribution coefficient λ of the white matter portion of the normal (healthy) brain 54, and it is determined, for example, on the basis of the hematocrit value (volume ratio of erythrocyte) H [%] of the specimen 12 inputted by the operator by the aid of the operation console 52. In this case, the hematocrit value H can be obtained from the blood of the specimen 12.

Figure 14:
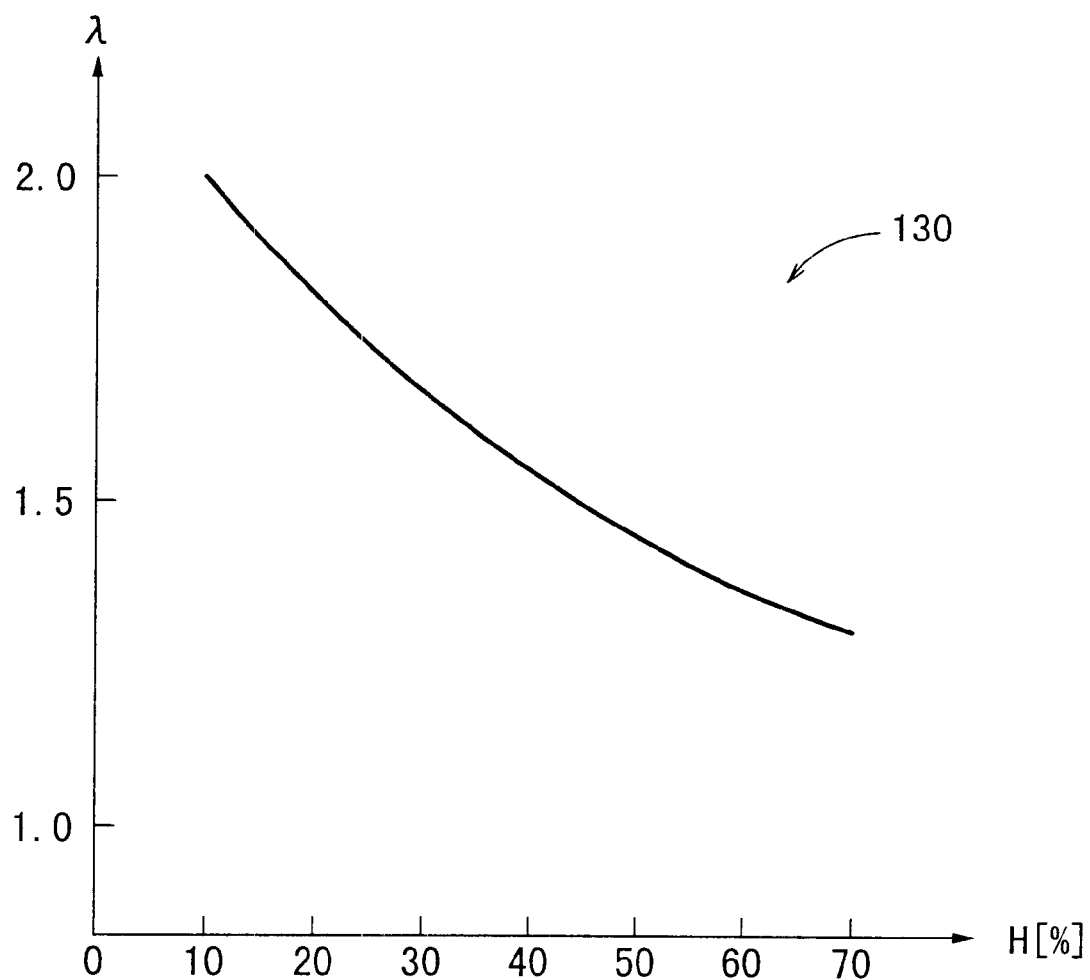
FIG. 14 shows an λ-H table.

The target value λτ is practically determined by retrieving a λ-H graph 130 shown in FIG. 14 with the hematocrit value H. The λ-H graph 130 is obtained by recording the relationship between the brain/blood distribution coefficient λ and the hematocrit value H at the white matter portion of the brain 54, as clarified by N. Veall et al. (see "The Partition of Trace Amounts of Xenon Between Human Blood and Brain Tissues at 37° C.", N. Veall et al., Phys. Med. Biol., 1965, Vol. 10, No. 3, 375–380).

In this case, it is also preferable that the target value λρ is obtained from the hematocrit value H by using a calculation expression to express the characteristic of the λ-H graph 130 shown in FIG. 14 and a table recorded with the characteristic.

It is known that the brain/blood distribution coefficient λ at the white matter portion of the brain 54 is about 1.5. Therefore, it is also preferable that the value (about 1.5) is set as the target value λτ.

As shown in FIG. 12, the γ value-establishing means 126 performs the processing to specify the true Ke/Ka conversion constant γ by comparing the temporary calculated values λα corresponding to the respective assumed values γα from the K-S-calculating means 124 with the target value λτ from the target λ value-calculating means 122. This processing may be started on the basis of a control signal to inform the fact that the last assumed value γα (for example, 2.5) is outputted from the assumed value-setting means 114.

Figure 15:
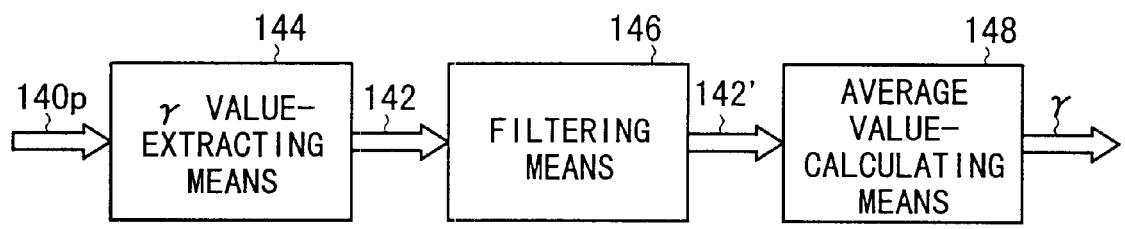
FIG. 15 shows a functional block diagram illustrating a means for specifying a true Ke/Ka conversion constant by using a target value as an index, in a γ value-establishing means which constructs the data processing means shown in FIG. 12.

FIG. 15 shows a functional block diagram illustrating means for specifying the true Ke/Ka conversion constant γ by using the target value λτ as an index {γ value (conversion constant)-extracting means 144, filtering means 146, average value-calculating means 148}.

Figure 16:
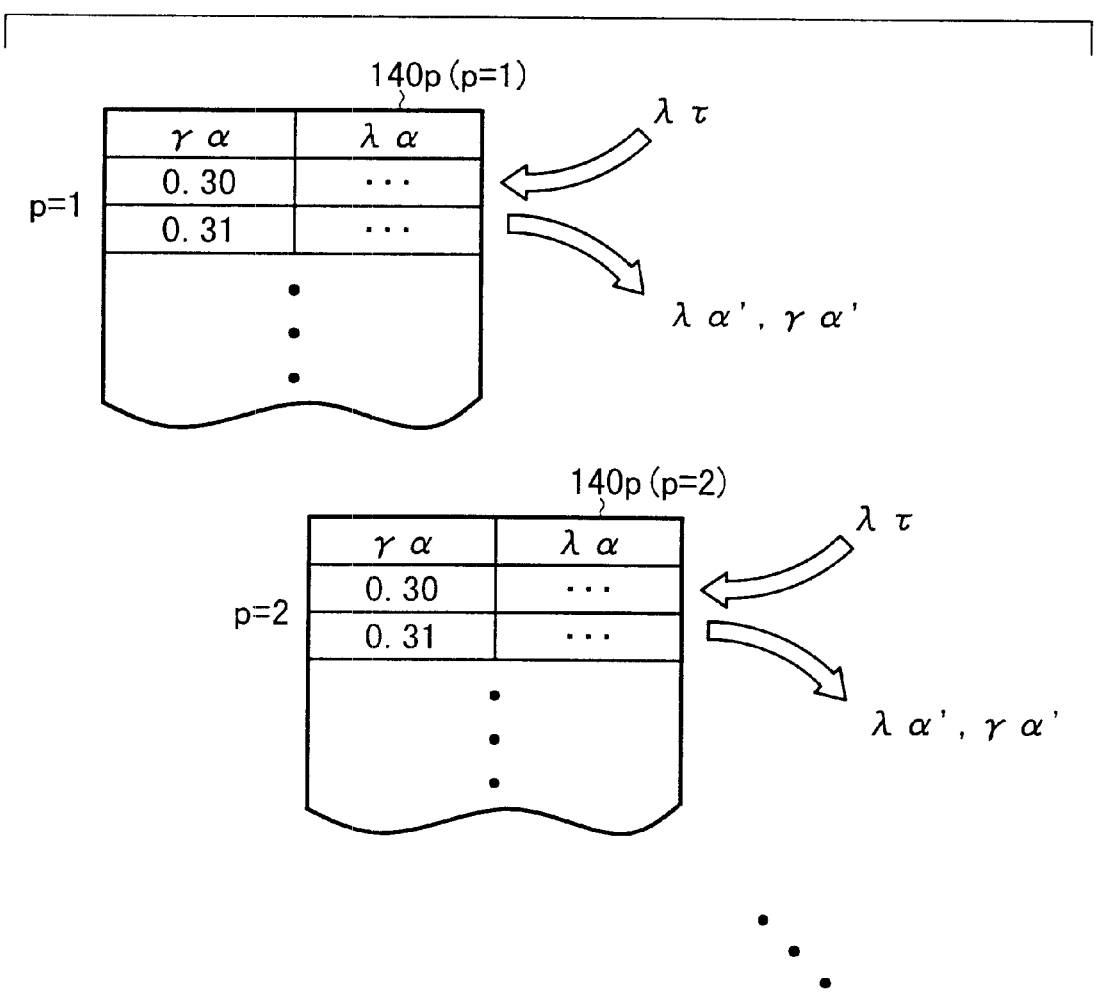
FIG. 16 shows tables in which temporary calculated values corresponding to respective assumed values are classified for each number of picture element.

As shown in FIG. 16, in the γ value-establishing means 126, the temporary calculated values λα corresponding to the respective assumed values γα from the K-S-calculating means are classified as tables 140p for each of the picture element numbers p (p=1, 2, . . . ). In the tables 140p, the temporary calculated values λα are classified for each of the assumed values γα.

As shown in FIGS. 15 and 16, γ value-extracting means 144 retrieves the temporary calculated value λα having the value which is the closest to the target value λτ, from the respective tables 140p by using the target value λτ. The retrieved temporary calculated value λα and the assumed value γα corresponding thereto (i.e., the assumed value γα with which the temporary calculated value λα most closely approaches the target value λτ) are extracted as the extracted temporary calculated value λα' and the extracted assumed value γα' respectively.

Figure 17:
FIG. 17 shows a table in which extracted temporary calculated values and extracted assumed values are classified for each number of picture element.

As shown in FIG. 17, after the extracting processing is performed, a table 142 is prepared, in which the extracted temporary calculated values λα' and the extracted assumed values γα' are classified for each of the picture element numbers p.

As shown in FIGS. 15 and 17, the filtering means 146 removes sets of the picture element numbers p, the extracted temporary calculated values λα', and the extracted assumed values γα' in which the extracted temporary calculated values λα' are deviated from a predetermined filtration range, from the obtained sets of the picture element numbers p, the extracted temporary calculated values λα', and the extracted assumed values γα' in the table 142. In this case, the filtration range is a range which is set on the basis of the target value λτ. For example, it is preferable to use a range having upper and lower limit values which are values (λτ±λτ×10%) obtained by addition or subtraction of a value of 10% of the target value λτ with respect to the target value λτ.

When the filtering processing is performed as described above, the set of the extracted temporary calculated value λα' and the extracted assumed value γα' corresponding to the white matter portion of the brain 54 is extracted as the filtered value.

Subsequently, the average value-calculating means 148 determines the average value of the extracted assumed values γα' in a table 142' obtained after the filtering processing performed by the filtering means 146 (i.e., average value of the extracted assumed values γα' corresponding to the white matter portion in the region of interest ROI). The average value is established as the true Ke/Ka conversion constant γ (true value).

Alternatively, the γ value-establishing means 126 shown in FIG. 12 may be used to obtain the extracted assumed value γα' as the assumed value γα obtained when the temporary calculated value λα is converged to the target value λτ (i.e., when the temporary calculated value λα satisfies the convergence condition based on the target value λτ) by vibrating the assumed value γα of the Ke/Ka conversion constant γ.

As shown in FIG. 12, the Ke/Ka conversion constant γ, which is obtained by the γ value-establishing means 126, is supplied to the Ka-storing means 116 and the output processing means 106 respectively.

The Ka-storing means 116 compares the respective assumed values γα from the assumed value-setting means 114 with the Ke/Ka conversion constant γ from the γ value-establishing means 126 to extract the assumed value γα which is coincident with the Ke/Ka conversion constant γ. The temporary calculated values Kaiα, Kaoα from the Ke/Ka conversion means 112, which correspond to the assumed value γα (i.e., which are determined by using the assumed value γα), are supplied as the true arterial blood velocity constants Kai, Kao to the f·λ-calculating means 104.

As shown in FIG. 11, the f·λ-calculating means 104 performs the calculation processing based on the use of the expressions (1) to (3) for each of the picture elements on the basis of the arterial blood velocity constants Kai, Kao from the γ-setting means 102 and the cerebral xenon gas concentration Cb(T) from the external storage unit 55 {cerebral xenon gas concentration Cb(T) obtained by the X-ray CT apparatus 14 at each of the points of time of measurement T}. The brain/blood distribution coefficient λ and the cerebral blood flow rate f of each of the picture elements obtained by the calculation processing are supplied to the output processing means 106.

The output processing means 106 prepares the display image data (display image data such as the f map Mf and the λ map Mλ described later on) to be displayed on the display unit 56 or to be outputted as the hard copy 57 from the printer 58, on the basis of the cerebral blood flow rate f and the brain/blood distribution coefficient λ from the f·λ-calculating means 104 and the Ke/Ka conversion constant γ from the γ-setting means 102.

FIGS. 18 to 21 show the screen 128 of the display unit 56.

Figure 18:
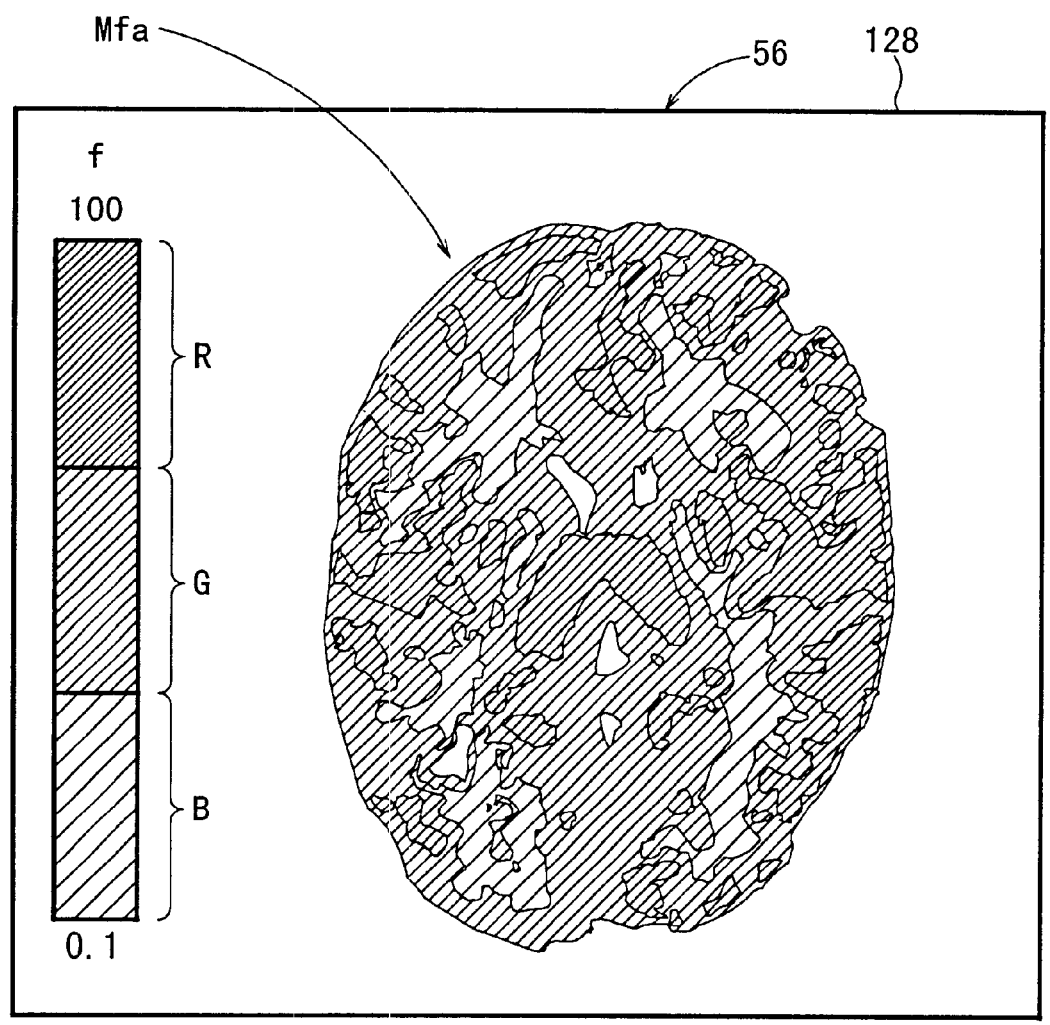
FIG. 18 shows an f map of brain displayed on a screen of a display unit.
Figure 19:
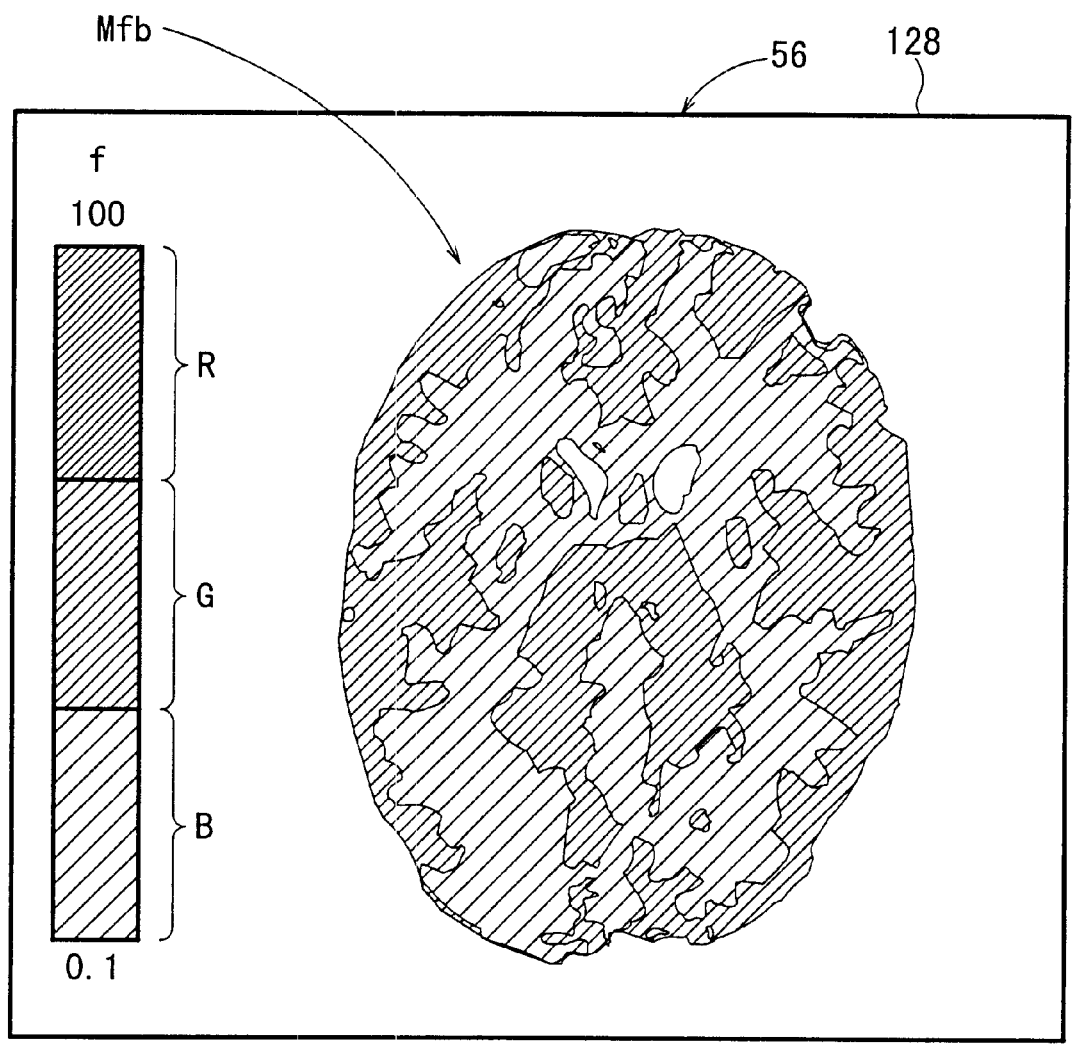
FIG. 19 shows an f map of brain displayed on the screen of the display unit.
Figure 20:
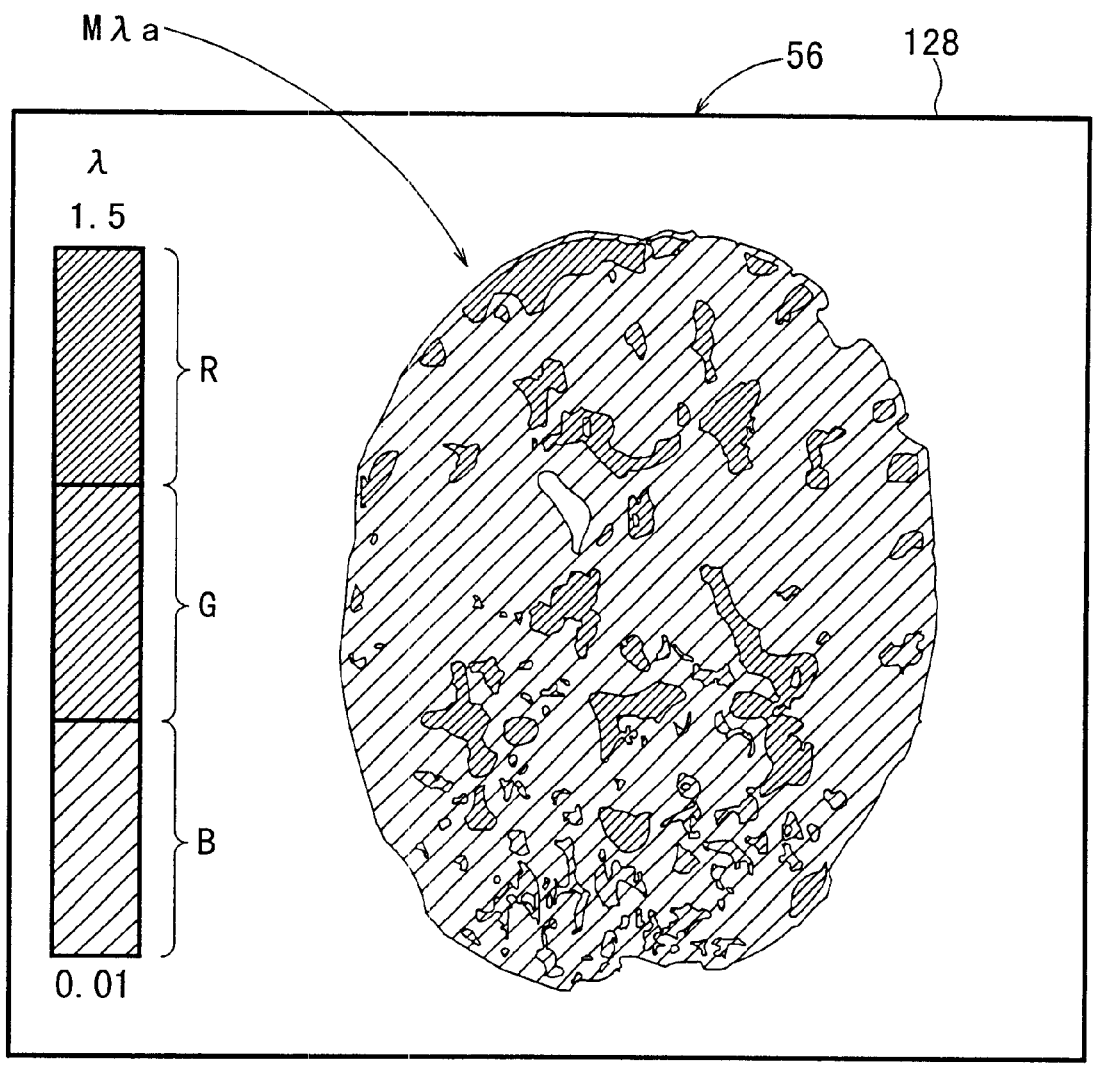
FIG. 20 shows a λ map of brain displayed on the screen of the display unit.
Figure 21:
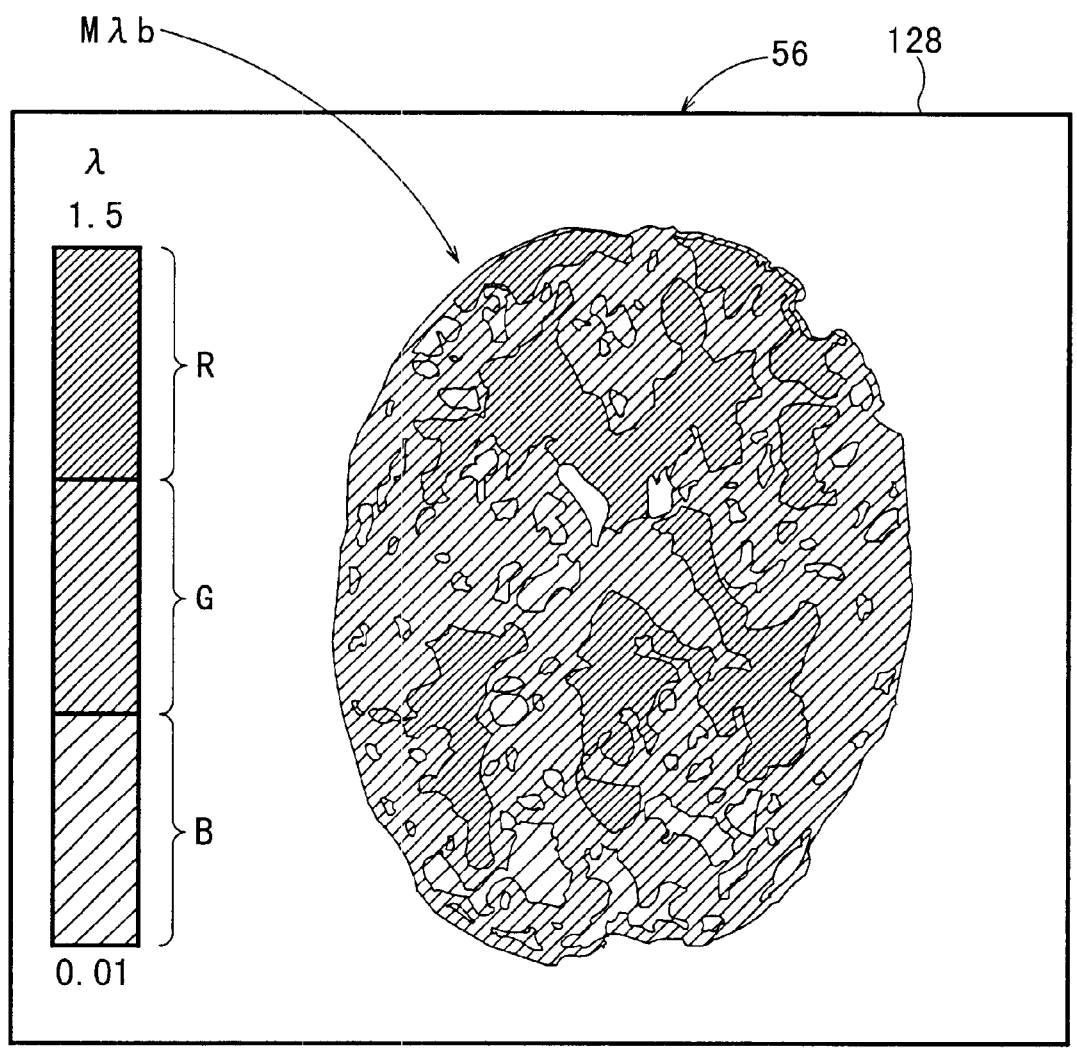
FIG. 21 shows a λ map of brain displayed on the screen of the display unit.

FIGS. 18 and 19 show f maps (distribution maps of the cerebral blood flow rate f) Mfa, Mfb of the brain 54, displayed in color on the screen 128 of the display unit 56. FIGS. 20 and 21 show λ maps (distribution maps of the brain/blood distribution coefficient λ) Mλa, Mλb of the brain 54, displayed in color on the screen 128 of the display unit 56.

In this case, FIGS. 18 and 20 show the f map Mfa and the λ map Mλa obtained when the correction is applied with the Ke/Ka conversion constant γ {i.e., when the arterial blood velocity constants Kai, Kao are obtained on the basis of the expressions (4) and (5)} when the arterial blood velocity constants Kai, Kao are obtained from the expiration gas velocity constants Kei, Keo respectively. On the other hand, FIGS. 19 and 21 show the f map Mfb and the λ map Mλb obtained when the correction is not applied with the Ke/Ka conversion constant γ {i.e., when there are given Kai=Kei and Kao=Keo in the expressions (4) and (5)} respectively.

The exemplary f maps Mfa, Mfb and the λ maps Mλa, Mλb shown in FIGS. 18 to 21 are obtained from a thirty-two years old healthy man as the specimen 12.

In the f map Mfa applied with the correction shown in FIG. 18, the cerebral blood flow rate f has the high value as compared with the f map Mfb which is not applied with the correction shown in FIG. 19. In the λ map Mλa applied with the correction shown in FIG. 20, the brain/blood distribution coefficient λ has the low value as compared with the λ map Mλb which is not applied with the correction shown in FIG. 21.

That is, when the correction based on the Ke/Ka conversion constant γ is not applied, then as shown in FIG. 10, the arterial blood velocity constants Kai, Kao are evaluated to be excessively large, the brain/blood distribution coefficient λ is evaluated to be excessively large. The cerebral blood flow rate f is evaluated to be excessively small.

On the contrary, when the correction based on the Ke/Ka conversion constant γ is applied, the excessively large evaluation disappears for the arterial blood velocity constants Kai, Kao and the brain/blood distribution coefficient λ. Thus, the appropriate value of the cerebral blood flow rate f is obtained.

As shown in FIG. 18, the blood flow rate per 100 g of brain, which is obtained from the f map Mfa applied with the application, is about 49.7 ml/100 g/min in the left hemisphere of the brain 54, and it is about 53.2 ml/100 g/min in the right hemisphere. These values are extremely close to the average blood flow rate per 100 g of brain of adult (about 54 ml/100 g/min). According to this fact, it is also understood that the value of the cerebral blood flow rate f depicted in the f map Mfa in FIG. 18 is appropriate.

The f maps Mfa, Mfb and the λ maps Mλa, Mλb shown in FIGS. 18 to 21 are displayed in color with three colors of R (red), G (green), and B (blue) respectively. However, the maps may be displayed in color with a larger number of colors (for example, thirteen colors).

As described above, in the embodiment of the present invention, the Ke/Ka conversion constant γ is determined by using the brain/blood distribution coefficient λ as the index. Further, when the arterial blood velocity constants Kai, Kao are determined from the expiration gas velocity constants Kei, Keo, the correction is applied on the basis of the Ke/Ka conversion constant γ. Accordingly, it is possible to correctly determine the cerebral blood flow rate f from the expiration gas xenon gas concentration Ce(t) which is used in place of the arterial xenon gas concentration Ca(t).

In this case, the Ke/Ka conversion constant γ is obtained by means of the extracting processing based on the target value λτ and the filtering processing. Therefore, it is possible to obtain the correct value of the Ke/Ka conversion constant γ.

The Ke/Ka conversion constant γ is obtained by means of the averaging processing which is directed to the region of interest ROI. Accordingly, it is possible to obtain the more correct value of the Ke/Ka conversion constant γ.

The target value λτ as the index is obtained on the basis of the hematocrit value H which is obtained from the blood of the specimen 12. Therefore, it is possible to provide the more reliable correctness for the obtained Ke/Ka conversion constant γ.

Figure 3:
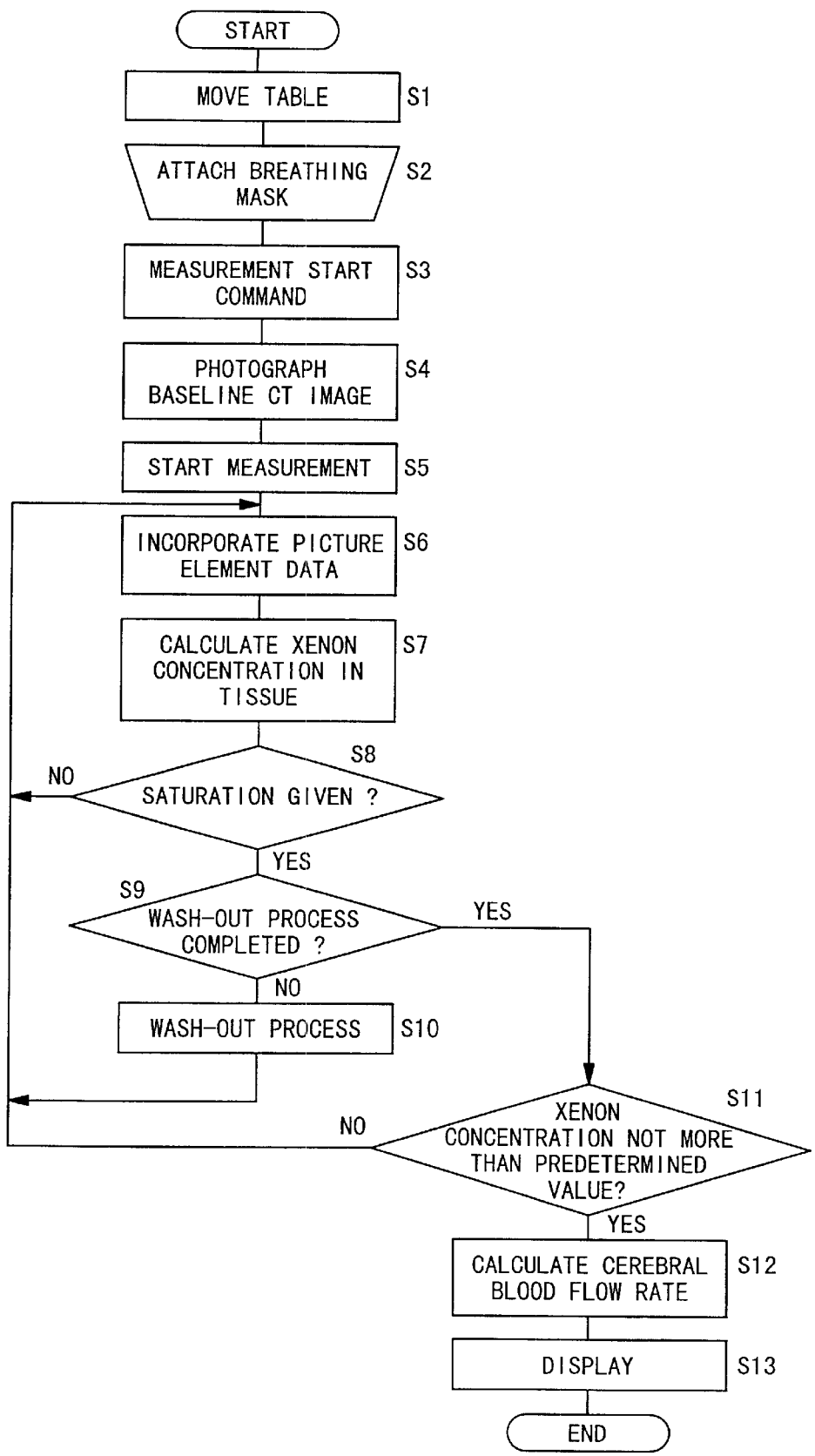
FIG. 3 shows a flow chart to be used to explain the operation of the embodiment of the present invention.

In the embodiment described above, the completion of the inhalation process of the xenon gas is judged by the saturation of the xenon gas concentration in the expiration gas (see the step S8 in the flow chart shown in FIG. 3), and the completion of the Wash-out process of the xenon gas performed by making the change into the inhalation of air is judged by the fact that the xenon gas concentration is not more than the predetermined value (see the step S11 in the flow chart shown in FIG. 3). However, the following time management is also available. That is, the inhalation process is completed for a predetermined period of time (for example, about 4 min), and the Wash-out process is completed for a predetermined period of time (for example, about 5 min).

The embodiment described above is not limited to the diagnosis of the head, which is also applicable to ordinary organs (internal organs) in which the arterial blood flow inflows and the blood outflows as the venous blood flow as in the head, for example, to examination sites such as the stomach, the bowels, the pancreas, and the liver.

As explained above, according to the present invention, the conversion constant γ is determined by using the brain/blood distribution coefficient λ as the index.

Therefore, it is possible to correctly determine the cerebral blood flow rate.

What is claimed is:

1. A method for determining a constant γ in a relational expression:

$$Ka = \gamma \times (1 - \exp(-Ke/\gamma))$$

wherein Ke represents an end-tidal air velocity constant and Ka represents an arterial blood velocity constant in a xenon CT examination, said method comprising:
   a step A of setting a region of interest (ROI) on a xenon CT image; and
   a step B of determining said constant γ with which a xenon distribution coefficient λ most closely approaches a predetermined target value in said preset region of interest.

2. The method for determining said constant according to claim 1, wherein in said step B, said distribution coefficient $\lambda$ is calculated by varying said constant $\gamma$ within a desired range from 0.24 to 7.7 to determine said constant $\gamma$ with which said distribution coefficient $\lambda$ most closely approaches said target value.

3. The method for determining said constant according to claim 2, wherein said desired range is a range from 0.3 to 2.5.

4. The method for determining said constant according to claim 1, wherein in said step B, said constant $\gamma$, with which a value of said distribution coefficient $\lambda$ most closely approaches said target value, is determined for each of predetermined picture elements included in said region of interest, and obtained values of said constant $\gamma$ are averaged to estimate an objective value of said constant $\gamma$.

5. The method for determining said constant according to claim 1, wherein:

in said step A, said region of interest is set to a region including cerebral white matter; and in said step B, said target value is determined depending on a hematocrit value.

6. A xenon CT apparatus comprising:

a gas supply unit for supplying xenon gas to a specimen;

a concentration-measuring unit for measuring a xenon gas concentration (hereinafter referred to as "expiration gas xenon gas concentration") in end-tidal air of said specimen;

a main X-ray CT apparatus body for obtaining CT image data of an examination site in order to obtain a xenon gas concentration (hereinafter referred to as "examination site xenon gas concentration") of said examination site of said specimen; and a data processing unit for determining said examination site xenon gas concentration on the basis of said CT image data, and determining a blood flow rate of said examination site on the basis of said examination site xenon gas concentration and said expiration gas xenon gas concentration, wherein:

said data processing unit determines a xenon gas distribution coefficient $\lambda$ between said examination site and blood of said specimen on the basis of a conversion constant $\gamma$ for converting a velocity constant (hereinafter referred to as "expiration gas velocity constant") of said expiration gas xenon gas concentration into a velocity constant (hereinafter referred to as "arterial blood velocity constant") of a xenon gas concentration (hereinafter referred to as "arterial xenon gas concentration") of blood flow in artery, and it establishes, as a true value, said conversion constant $\gamma$ with which said distribution coefficient $\lambda$ most closely approaches a predetermined target value.

7. The xenon CT apparatus according to claim 6, wherein:

said data processing unit includes a conversion constant-setting means for determining said conversion constant $\gamma$; and said conversion constant-setting means has an assumed value-setting means for setting an assumed value of said conversion constant $\gamma$ and varying said assumed value.

8. The xenon CT apparatus according to claim 7, wherein said conversion constant-setting means includes:

a temporary velocity constant-setting means for determining a temporary calculated value of said arterial blood velocity constant from said expiration gas velocity constant on the basis of said assumed value of said conversion constant $\gamma$;

a temporary distribution coefficient-calculating means for determining a temporary calculated value of said distribution coefficient $\lambda$ from said temporary calculated value of said arterial blood velocity constant and said examination site xenon gas concentration; and a conversion constant-extracting means for extracting, as an extracted assumed value to be established as said true value, an assumed value of said conversion constant $\gamma$ corresponding to one which most closely approaches said target value, of respective temporary calculated values of said distribution coefficient $\lambda$ obtained on the basis of respective assumed values of said conversion constant $\gamma$.

9. The xenon CT apparatus according to claim 8, wherein said conversion constant-setting means includes a filtering means for determining, as a filtered value to be established as said true value, one in which said temporary calculated value of said distribution coefficient $\lambda$ corresponding to said extracted assumed value is included in a predetermined filtration range, of said extracted assumed values.

10. The xenon CT apparatus according to claim 9, wherein said conversion constant-setting means includes:

an ROI data-extracting means for extracting examination site xenon gas concentrations respectively obtained on the basis of data corresponding to a plurality of predetermined picture elements, of data of respective picture elements included in said CT image data; and an average value-calculating means for determining, as said true value of said conversion constant $\gamma$, an average values of said filtered values obtained on the basis of said extracted examination site xenon gas concentrations respectively.

11. The xenon CT apparatus according to claim 7, wherein said assumed value-setting means varies said assumed value of said conversion constant $\gamma$ within a desired range from 0.24 to 7.7.

12. The xenon CT apparatus according to claim 11, wherein said desired range is a range from 0.3 to 2.5.

13. The xenon CT apparatus according to claim 7, wherein:

said conversion constant-setting means has a target value-calculating means for determining said target value; and said target value-calculating means determines said target value depending on a hematocrit value when said examination site is brain of said specimen, and a region of interest for determining said conversion constant $\gamma$ is set to be a region including white matter of said brain.

14. The xenon CT apparatus according to claim 6, wherein a relational expression for determining said arterial blood velocity constant from said expiration gas velocity constant on the basis of said conversion constant $\gamma$ is represented by:

$$Ka = \gamma \times (1 - \exp(-Ke/\gamma))$$

wherein Ke represents said expiration gas velocity constant, and Ka represents said arterial blood velocity constant.

15. The xenon CT apparatus according claim 6, further comprising a display unit for displaying a distribution map of said blood flow rate and/or said conversion constant $\gamma$.

* * * * *